… … …

United States Patent [19]

Brunner et al.

[11] Patent Number: 5,783,680

[45] Date of Patent: Jul. 21, 1998

[54] GENETIC DIAGNOSIS AND TREATMENT FOR IMPULSIVE AGGRESSION

[75] Inventors: H. G. Brunner, Nijmegen, Netherlands; Xandra O. Breakefield, Newton, Mass.

[73] Assignees: The General Hospital Corporation, Boston, Mass.; Stichting Katholieke Universiteit, Netherlands

[21] Appl. No.: 132,168

[22] Filed: Oct. 6, 1993

[51] Int. Cl.[6] .................... C12N 15/53; C12N 15/12; C12N 15/74; C12N 15/79

[52] U.S. Cl. .................... 536/23.2; 536/23.5; 435/252.3; 435/320.1

[58] Field of Search .................... 435/189, 172.3, 435/252.3, 320.1; 536/23.2, 23.5

[56] References Cited

U.S. PATENT DOCUMENTS 5,030,570  7/1991  Breakefield et al. .................... 435/189

FOREIGN PATENT DOCUMENTS

WO 90/00195  1/1990  WIPO .
WO 93/05783  4/1993  WIPO .

OTHER PUBLICATIONS

Berger, W., et al., "Isolation of a candidate gene for Norrie disease by positional cloning," *Nature Genetics* 1:199–203 (Jun. 1992).

Bleeker-Wagemakers, E.M. et al., "Norrie Disease as Part of a Complex Syndrome Explained by a Submicroscopic Deletion of the X-Chromosome", *Opthalamic Paediatr. Genet.* 9(3):137–142 (1992).

Brunner, H.G. et al., "X-Lined Borderline Mental Retardation with Prominent Behavioral Disturbance: Phenotype, Genetic Localization, and Evidence for Disturbed Monoamine Metabolism," *Am. J. Hum. Genet.* 52:1032–1039 (1993).

Brunner et al., "Abnormal Behavior Linked to a Point Mutation in the Structural Gene for Monoamine Oxidase A," *Am. Soc. for Hum. Genet.* 53 (3), Abs. 13 (Sep. 1993).

Chen, Z–Y. et al., "Organization of the Human Monoamine Oxidase Genes and Long-Range Physical Mapping around Them," *Genomics* 14:75–82 (1992).

Chen, Z–Y. et al., "Structure of the Human Gene for Monoaimine Oxidase Type A, " *Nucleic. Acids Research* 19(16): 4537–4541 (1991).

Coccaro, E.F., "Central Serotonin and Impulsive Aggression," *British J. Psychiatry* 155 (Supp. 8): 52–62 (1989).

Collins, F.A., et al., "Clinical, Biochemical, and Neuropsychiatric Evaluation of a Patient With a Contiguous Gene Syndrome due to a Microdeletion Xp11.3 Including the Norrie Disease Locus and Monoamine Oxidase (MAOA and MAOB) Genes," *Am. J. Med. Genetics* 42:127–134 (1992).

de la Chapelle, A. et al., "Norrie disease caused by a gene deletion allowing carrier detection and prenatal diagnosis," *Clin. Genet.* 28:317–320 (1985).

Dialog Search 0145760, Breakefield, X.O. et al., "Biochemical and Genetic Analysis of Monoamine Oxidase", *Federal Research in Progress* (1993).

Donnai, D. et al., "Norrie disease resulting from a gene deletion: clinical features and DNA studies," *J. Med. Genet.* 25:73–78 (1988).

(List continued on next page.)

*Primary Examiner*—Robert A. Wax
*Assistant Examiner*—William W. Moore
*Attorney, Agent, or Firm*—Sterne, Kessler, Goldstein & Fox P.L.L.C.

[57] ABSTRACT

Monamine oxidase genes and proteins associated with abnormal behavior are provided. Cells and non-human transgenic animals comprising at least one mutant monamine oxidase gene, and purified mutant monamine oxidase protein are also provided. The genes, cells and proteins of the invention are useful in the and therapeutic and diagnostic methods provided which relate to treating and diagnosing individuals having a mutant monamine oxidase gene and exhibiting an associated abnormal behavior.

10 Claims, 1 Drawing Sheet

OTHER PUBLICATIONS

Hotamisligil, G.S. et al., "Human Monoamine Oxidase A Gene Determines Levels of Enzyme Activity," *Am. J. Hum. Genet.* 49:383–392 (1991).

Hsu, Y–P.P. et al., "Structural Features of Human Monoamine Oxidase A Elucidated from cDNA and Peptide Sequences," *J. Neurochem.* 51 (4):1321–1323 (1988).

Hsu, Y–P.P. et al., "Molecular Genetics of the Monoamine Oxidases," *J. Neurochem.* 53 (1):12–18 (1989).

Kwiatkowski, D.J. et al., "Torsion Dystonia Genes in Two Populations Confined to a Small Region on Chromosome 9q32–34," *Am. J. Hum. Genet.* 49:366–371 (1991).

Morrell, V., "Evidence Found for a Possible 'Aggression Gene'," *Science* 260:1722–1723 (18 Jun. 1993).

Murphy, D.L. et al., "Marked Amine and Amine Metabolite Changes in Norrie Disease Patients with an X–Chromosomal Deletion Affecting Monoamine Oxidase," *J. Neurochem.* 54 (1):242–247 (1990).

Orita, M., et al., "Detection of polymorphisms of human DNA by gel electrophoresis as single-stranded conformation polymorphisms," *Proc. Natl. Acad. Sci. USA* 86:2766–2770 (Apr. 1989).

Richardson, S., "A Violence in the Blood," *Discover*:30–31 (Oct. 1993).

Tivol, E., "A Rapid PCR–based Method For Screening the Human MAOA Gene for Exonic Mutations," *Am. Soc. for Hum. Genet.* 53(3), Abs. 1632 (Sep. 1993).

van den Ouweland, A.M.W. et al., "Mutations in the vasopressin type 2 receptor gene (AVPR2) associated with nephrogenic diabetes insipidus," *Nature Genetics* 2:99–102 (Oct. 1992).

Zhu, D. et al., "Microdeletion in the X–Chromosome and Prenatal Diagnosis in a Family With Norrie Disease," *Am. J. Med. Genet.* 33:485–488 (1989).

Wu, H.–F., et al., Molecular Pharmacology, vol. 43, No. 6, "Site–Directed Mutagenesis of Monoamine Oxidase A and B: Role of Cysteines", pp. 888–893, Jun. 1993.

Gottowik, J., et al., FEBS Letters, vol. 317, Nos. 1 and 2, "Characterization of wild–type and mutant forms of human monoamine oxidase A and B expressed in a mammalian cell line", pp. 152–156, Feb. 1993.

Hendriks, R. W., et al., Immunodeficiency, vol. 4, Nos. 1–4, "Carrier Detection in X–Linked Immunodeficiencies I: A PCR–based X Chromosome Inactivation Assay at the MAOA Locus", pp. 209–211, Jan. 1993.

Shih, J. C., et al., Journal of Psychiatry and Neuroscience, vol. 18, No. 1, "Structure and Promoter Organization of the Human Monoamine Oxidase A and B Genes", pp. 25–32, Jan. 1993.

5,783,680

1

GENETIC DIAGNOSIS AND TREATMENT FOR IMPULSIVE AGGRESSION

STATEMENT AS TO RIGHTS TO INVENTIONS MADE UNDER FEDERALLY-SPONSORED RESEARCH AND DEVELOPMENT

Part of the work performed during the development of this invention utilized U.S. Government Funds under Grant No. NS 21921 from The National Institutes Of Health (NIH). The government may have certain rights in this invention.

BACKGROUND OF THE INVENTION

1. Field of the Invention

The present invention relates generally to substantially purified monamine oxidase genes and proteins that are associated with abnormal behavior. The invention also relates to substantially purified mutant monamine oxidase genes, oligonucleotides and primers derived from monamine oxidase genes, cell lines comprising at least one monamine oxidase gene, and to purified mutant monamine oxidase protein. The invention further relates to diagnostic methods including, methods for determining carriers of a monamine oxidase gene defect, and methods for determining the presence of a monamine oxidase gene defect in cells and in individuals. The invention also relates to non-human transgenic animals and therapies using monamine oxidase proteins and genes.

2. Description of the Background Art

Etiology of Abnormal Behavior

Studies of aggressive behavior in animals and humans have implicated altered metabolism of serotonin (Valzelli, L., *Pharmacol. Res. Commun.* 14:1 (1982); Valzelli, L., *Psychobiology of Aggression and Violence*, Raven Press, New York, (1981); Cocarro, E. F., Br. *J. Psychiatry* 155 (Suppl. 8):52 (1989); Higley, J. D. et al., *Arch. Gen. Psychiatry* 49:436 (1992); Troncone, L. R. P. et al., *Physiol. Behav.* 50:173 (1991); Brown, G. L. et al., *Psychiatry Res.* 1:131 (1979); Linnoila, M. et al., *Life Sci.* 33:2609 (1983); Kantak, K. M. et al., *Pharmacol. Biochem. Behavior* 12:173 (1980); Kruesi, M. J. P. et al., *Arch. Gen. Psychiatry* 47:419 (1990); Popova, N. K. et al., *Aggress. Behav.* 17:207 (1991)), and to a lesser extent of dopamine (Troncone, L. R. P. et al., *Physiol. Behav.* 50:173 (1991); Nikulina, E. M. et al., *Aggress. Behav.* 18:65 (1992); Tufik, S. et al., *Pharmacol.* 16:98 (1978)), and of noradrenaline (Higley, J. D. et al., *Arch. Gen. Psychiatry* 49:436 (1992); Troncone, L. R. P. et al., *Physiol. Behav.* 50:173 (1991); Brown, G. L. et al., *Psychiatry Res.* 1:131 (1979); Reis, D. J., *Ass. Res. Nerv. Ment. Dis.* 50:266 (1972); Eichelman, B. et al., *Biol. Psychiatry* 6:143 (1973); Winslow, J. T. et al., *Psychopharmacol.* 81:286 (1983)). No genetic mutations or genetic defects in the metabolism of these neurotransmitters that affect aggressive behavior have been reported.

Genetic Defects of Monamine Oxidase

A large kindred, in which several males are affected by a syndrome of borderline mental retardation and abnormal behavior, including disturbed regulation of impulsive aggression has been described (Brunner, H. G. et al., *Am. J. Hum. Genet.* 52:1032 (1993)). The genetic defect for this condition was assigned to the p11-p21 region of the X chromosome, in the general vicinity of the genes for monoamine oxidase A and B. Since monamine oxidase A and monamine oxidase B are known to metabolize serotonin, dopamine and noradrenaline, these patients were evaluated for monamine oxidase deficiency by testing levels of amine metabolites. Moreover, monamine oxidase B activity is normal in affected males from this family (Brunner, H. G. et al., *Am. J. Hum. Genet.* 52:1032 (1993)).

SUMMARY OF THE INVENTION

Recognizing the importance of devising novel methods and reagents useful in diagnosis and therapy of abnormal behavior, the inventors have investigated genetic mutations associated with abnormal behavior, especially impulsive aggressive behavior.

These efforts led to the discovery of a genetic mutation in the monamine oxidase gene associated with behavioral pathologies, and have allowed for the development of methods useful for detection of carriers, diagnosis of the pathologies, and therapies for those afflicted with impulsive aggressive disorders.

Accordingly, one object of the present invention is to provide an isolated monamine oxidase gene comprising a mutation of at least one nucleotide and vectors created thereby.

A further object of the present invention is to provide a oligonucleotides and primers complementary to a monamine oxidase gene or transcript.

The invention also provides a cell line comprising a monamine oxidase gene comprising a mutation of at least one nucleotide.

The invention further provides a substantially purified mutant monamine oxidase protein.

Another object of the invention is to provide methods for determining whether an individual is a carrier of a mutant monamine oxidase gene or has a disease state associated with a mutant monamine oxidase gene. The isolated genes, oligonucleotides, primers, cell lines and substantially purified proteins of the invention are useful in the methods of the invention, as well as in methods known in the art.

The invention further provides methods for determining the presence of a mutant monamine oxidase gene in cells from an individual suspected to contain a mutant monamine oxidase gene.

The invention still further provides methods for determining monamine oxidase deficiency in an individual exhibiting impulsive aggression in order to diagnose a genetic basis for the behavior.

The invention is also directed to immunological methods for the detection of mutant monamine oxidase in bodily tissue, and provides kits useful in these immunological methods.

The invention is still further directed to non-human transgenic animals substantially all of whose somatic and germ cells comprise and express a gene coding for monamine oxidase.

The invention is also directed to treatments and therapies by which normal monamine oxidase protein or gene is introduced into individuals who have congenital monamine oxidase defects or mutations.

DESCRIPTION OF THE PREFERRED EMBODIMENTS

Introduction

Figure 1:
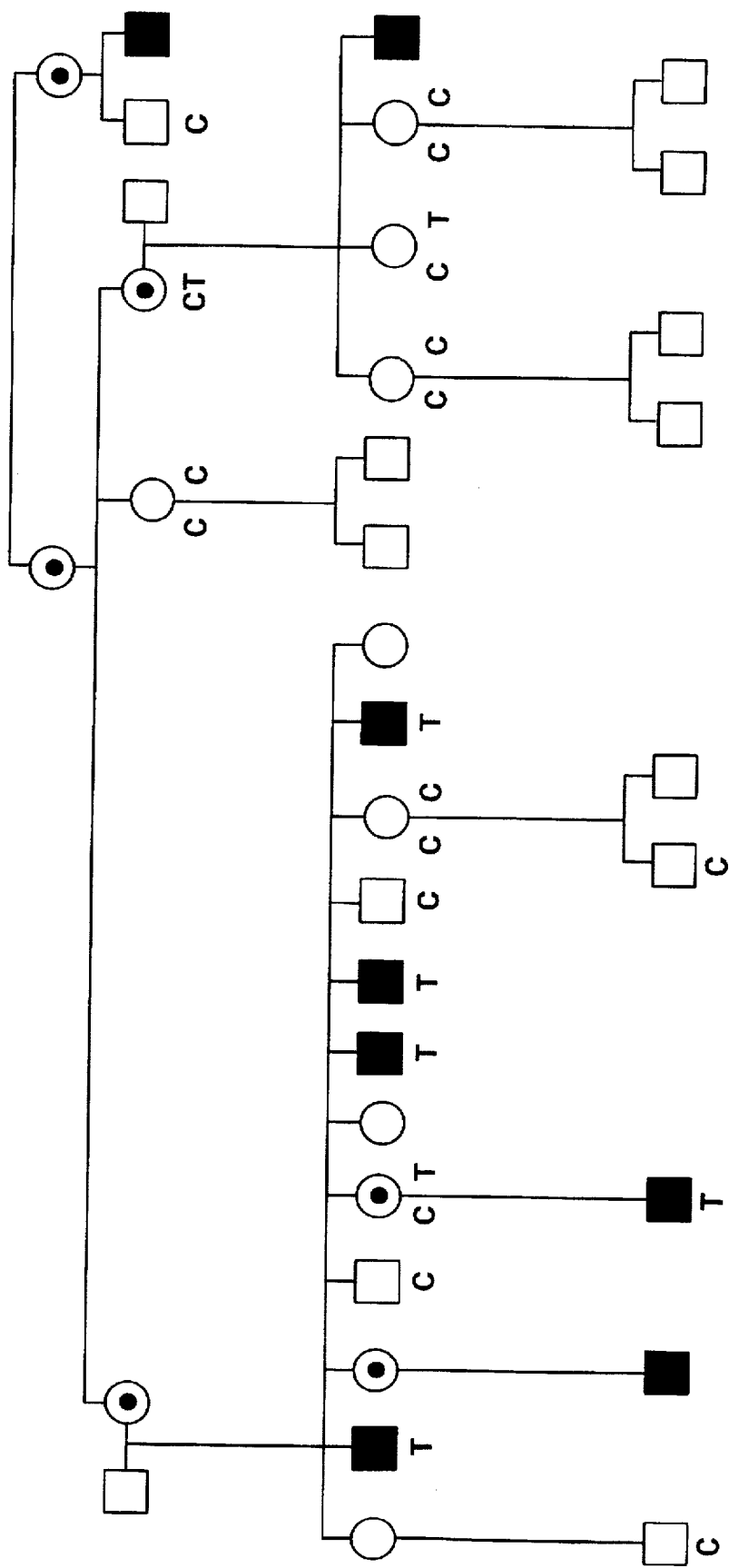
FIG. 1 shows segregation of a mutation in the monamine oxidase A structural gene in a family with X-linked borderline mental retardation and prominent behavioral disturbance. All affected males and obligate carriers have a C to T mutation at nucleotide 936. In 12 normal males, only the normal C is present.

The inventors have discovered complete and selective deficiency of monamine oxidase A in humans, and that selective deficiency results in a marked disturbance of monamine metabolism correlating to and associated with aggressive behavior. Based on this discovery, the present invention is directed to compositions and methods useful for therapy and for diagnosis of behavioral disorders associated with monamine oxidase deficiency. The invention is further directed to isolated mutant monamine oxidase genes, analogues, and oligonucleotides and primers derived from isolated mutant and normal monamine oxidase genes. The invention further provides vectors, cell lines and non-human transgenic animals comprising at least one isolated monamine oxidase gene comprising a mutation of at least one nucleotide useful in the methods of the present invention as well as its methods known in the art. The invention also provides substantially purified mutant monamine oxidase proteins. The isolated genes, substantially purified protein, oligonucleotides, primers, vectors, cell lines and non-human transgenic animals of the present invention are useful in the methods of the present invention as well as in methods known in the art.

Moreover, methods for determining whether an individual is a carrier of a mutant monamine oxidase gene or has a disease state associated with a mutant monamine oxidase gene, methods for determining the presence of a monamine oxidase gene defect in a cell, and methods useful for determining monamine oxidase deficiency in an individual are provided as described below.

I. Monamine Oxidase Genes, Vectors, Oligonucleotlides, and Primers

As used herein, the term "gene" refers generally to a DNA, cDNA or rDNA molecule encoding an RNA, mRNA and/or protein. As used herein, the term "gene" also refers to a pseudogene incapable of encoding RNA, mRNA or protein but which may comprise sequences or motifs that normally mediate transcription, translation, splicing, polyadenylation or other aspects of gene expression or pseudogene sequences that are analogues to sequences or motifs which normally mediate various aspects of gene expression but are non-functional. The term "gene" further refers to molecules that encode proteins having normal, altered or no function. Moreover, the term "gene" encompasses molecules which comprise unmodified DNA and DNA comprising modified bases, including, for example, methylated bases.

As used herein, the term "normal" refers generally to that state of an individual, a behavior, or a molecule which is ordinary, wild-type, common, without defect or affect, and not mutant. As used herein to refer to a molecule, the term "normal" also refers generally to sequences or structures that, while they may vary from a canonical sequence or structure, comprise neutral polymorphisms and do not vary in function from a molecule having a non-mutant sequence or structure.

As used herein, the term "individual" refers generally to a single specimen or member of an organism-group or species. The term is to be construed to encompass, but not be limited to, mammals, birds, reptiles and amphibians, but is especially directed to humans.

The term "carrier" as used herein refers generally to individuals who have a mutant genotype for a genetic characteristic but do not exhibit a mutant phenotype and thus fall within control ranges in experiments if compared to normal individuals. For example, the term may refer to an individual who has a genetic mutation on one member of a gene pair or locus and is phenotypically normal, but the same mutation being present on both members would render the individual phenotypically abnormal. In a further example, the term may refer to an X-linked disorder wherein a female individual who has a genetic mutation on both members of a gene pair or locus is phenotypically normal and is a carrier, but the same mutation being present on one member in a male individual would render that individual phenotypically abnormal.

The term "monamine oxidase deficiency" as used herein refers generally to the absence of, lowered levels of, or altered kinetic properties of, monamine oxidase or monamine oxidase activity in cells or individuals if compared to control cells or normal individuals.

As used herein, the term "substantially pure" or "substantially purified" is meant to describe a compound which is substantially free of any compound associated with the compound in its natural state. For example, a protein or gene which is substantially free from other proteins, nucleic acids, lipids and carbohydrates is considered to be substantially pure or purified. The term is further meant to describe a compound which is homogeneous by one or more criteria of purity or homogeneity used by those of skill in the art. The terms "substantially pure" or "substantially purified" as used herein are not meant to exclude artificial, synthetic, or semi-synthetic mixtures or hybrids.

As used herein, the term "decreased activity" refers generally to that state of a protein or enzyme wherein such protein or enzyme exhibits either no or lowered enzyme kinetics, no or lowered levels by virtue of no or lowered gene expression from the associated gene, or no or lowered protein function. Decreased activity may be caused by, for example, any genetic mutation that will alter protein structure, including mutant stop codons, mutant amino acid codons and codon deletions. The term decreased activity shall be construed to include alterations in activity caused by genetic mutations that are capable of altering gene expression or function.

As used herein, the term "truncated" is meant to describe a protein having normal amino-terminus but an abnormal, foreshortened carboxyterminus. For example, a stop codon mutant upstream of the normal stop codon would encode a truncated protein.

The present invention provides an isolated monamine oxidase gene comprising a mutation of at least one nucleotide. A preferred embodiment of the present invention provides an isolated monamine oxidase gene which is the monamine oxidase A gene (SEQ ID NO:31). A more preferred embodiment provides a monamine oxidase A gene which comprises a mutation in exon 8 (SEQ ID NO:33), and particularly, but not limited to, a C to T mutation in exon 8 at nucleotide 936 which creates an in-frame termination codon. The present invention further provides a monamine oxidase A gene which encodes a truncated protein about 296 amino acids in length.

As used herein, the term "expression" or "expressing" refers generally to any manifestation of gene function, including, for example, transcription of RNA, processing of RNA into mRNA, and translation of mRNA into protein.

The present invention provides an isolated monamine oxidase A gene which is capable of expressing a decreased amount of monamine oxidase protein in a mammalian cell, and an isolated monamine oxidase A gene which is capable of expressing a monamine oxidase protein having lowered activity. A preferred embodiment of the present invention provides an isolated monamine oxidase A gene that comprises a mutation associated with abnormal behavior in an individual.

The isolated monamine oxidase genes of the present invention will be useful in many techniques of nucleic acid hybridization known and employed in the art, such as for example, Northern and Southern blotting and PCR. For examples of nucleic acid hybridization techniques, see Meinkoth, J. et al., *Anal. Biochem.* 138:267–284 (1984); Haymes, et al. (In: Nucleic Acid Hybridization, A Practical Approach, IRL Press, Washington, D.C. (1985), and Sambrook, et al., *Molecular Cloning—A Laboratory Manual*, (Second Edition), Cold Spring Harbor Labs (1989), all three of which are incorporated by reference herein. The monamine oxidase genes of the present invention will also be useful to construct the various expression and cloning vectors of the present invention. The expression vectors of the invention will allow the production of useful quantities of substantially purified monamine oxidase protein in various cells and cell lines. The isolated genes will also be useful in in vitro transcription (See, for example, Melton, et al., *Nucl. Acids Res.* 12:7035–7056 (1984)) and translation systems. Fusion constructs can be easily made by those skilled in the art using methods well known in the art for preparing fusion proteins. Such fusion protein gene constructs will be useful in methods of immunopurification known in the art. See, for example, Sambrook et al., *Molecular Cloning—A Laboratory Manual*, (Second Edition), Cold Spring Harbor Labs (1989).

It is contemplated that isolated substantially purified mutant monamine oxidase genes of the invention will be useful for introduction into an organism so as to make a transgenic organism. It is also contemplated by the present invention that a transgenic organism expressing a mutant monamine oxidase gene will be useful in further dissecting the etiology of the associated abnormal behavior and in the rational design of novel therapies for treatment of the metabolic disturbance caused by the monamine oxidase deficiency state. It is still further contemplated that such therapies will be useful to relieve the associated behavioral disorders associated with monamine oxidase deficiency. Moreover, animal models will be useful to determine the various neurochemical alterations that are induced by selective monamine oxidase A deficiency and their secondary effects on the organism. It is also contemplated that the transgenic animals will be useful to study developmental abnormalities in the morphology or heteroanatomy of the nervous system affected by the mutant gene.

The invention further provides an oligonucleotide and primers derived from an isolated monamine oxidase gene SEQ ID NO:31). It is preferred that the oligonucleotides and primers be from the monamine oxidase A gene. It is more preferred that the primers of the invention be capable of detecting a mutation in a monamine oxidase A gene. It is most preferred that the primers capable of detecting a mutation in a monamine oxidase A gene comprise a sequence consisting essentially of a sequence selected from the group consisting of: AGTTGATAGAAGGGTCCTTC (SEQ ID NO:1); CAGGCCACTGCTACGGTCCACAC (SEQ ID NO:2); GGAACCAATTTTTCTCTTTT (SEQ ID NO:3); TCACTTGGGTGAAAAGTCAG (SEQ ID NO:4); TATGTTCTAGGGGAAACA (SEQ ID NO:5); ACACATTTACCTCCTTCCC (SEQ ID NO:6); AGAGGTGGCAGTTACCATCA (SEQ ID NO:7); AATTTTGAATGGTCAAGTCT (SEQ ID NO:8); ATTGCAACAGAAAAACTT (SEQ ID NO:9); AGAAAGCAAAATCACAGA (SEQ ID NO: 10); CTTTCTTACCTACCTCCTC (SEQ ID NO:11); ACTGAGTTACCTCATAATG (SEQ ID NO:12); GACTGCAGCTCACATCTGAGG (SEQ ID NO:13); ACCTCCTGTTCAATAATC (SEQ ID NO:14); CCCATTGATTTTTCTCCT (SEQ ID NO:15); ATGCAGAAGACCCTGTCTAAC (SEQ ID NO:16); ACAGCTGTAACCTGATCATTC (SEQ ID NO:17); AGCAAAATACAAAAGGTT (SEQ ID NO:18); TTTTTTTTTTGGCTCTGTT (SEQ ID NO:19); TGCTTTGCTTTACTACTT (SEQ ID NO:20); TTTGTTAAAGCAACTATA (SEQ ID NO:21); AATTTGCACTGAACTCTG (SEQ ID NO:22); AGTCATACGGGTGTTTTT (SEQ ID NO:23); CCTTCCCGAGACCATTTA (SEQ ID NO: 24); GAAAGCCCAGGCTCTCTC (SEQ ID NO:25); ATAGTGCCCAGAGTCACCAA (SEQ ID NO:26); GACGTTCCAGAGGTAGAAAT (SEQ ID NO:27); ACATGAGTGATCTACACTG (SEQ ID NO:28); CGACCTTGACTGCCAAGAT (SEQ ID NO:29); and CTTCTTCTTCCAGAAGGC (SEQ ID NO:30).

Oligonucleotides and primers of the present invention will be useful as probes to detect monamine oxidase genes, and in particular mutant monamine oxidase genes, especially mutant monamine oxidase A genes. Oligonucleotides and primers of the invention will also be useful in nucleic acid hybridization techniques. See for example, Haymes, B. D., et al. (In: Nucleic Acid Hybridization, A Practical Approach. IRL Press, Washington, D.C. (1985); and Sambrook et al., *Molecular Cloning—A Laboratory Manual*, (Second Edition), Cold Spring Harbor Labs (1989). The oligonucleotides and primers will further be useful as primers for cDNA synthesis and PCR. Moreover, primers are provided which allow PCR to be performed across all exons of the monamine oxidase A gene.

It is contemplated by the present invention that the oligonucleotides and primers will be particularly useful in the methods of the invention. For example, the oligonucleotides and primers will be useful in methods for determining whether an individual is a carrier of a monamine oxidase gene defect, methods for determining the presence of a monamine oxidase gene defect in a cell, and methods for determining monamine oxidase deficiency in an individual. Moreover, one skilled in the art will recognize that the oligonucleotides and primers of the present invention can be readily adapted to be used as probes for a variety of purposes and used in methods known and employed in the art.

II. Cell Lines Having Genetic Mutations in Monamine Oxidase Genes

The present invention provides a cell line comprising a monamine oxidase gene comprising a mutation of at least one nucleotide. A preferred embodiment of the present invention provides a cell line comprising a monamine oxidase A gene (SEQ ID NO:31). A more preferred embodiment provides a cell comprising a gene a comprising a mutation in exon 8 SEQ ID NO:33), and particularly, but not limited to, a C to T mutation in exon 8 at nucleotide 936 which creates an in-frame termination codon. The further preferred embodiment provides a cell line comprising a monamine oxidase A gene which encodes a truncated protein about 296 amino acids in length.

The present invention provides prokaryotic and eukaryotic cells and cell lines comprising monamine oxidase genes. The eukaryotic cells will include, but not be limited to, mammalian cells, avian cells, reptilian cells and amphibian cells, but the invention is especially directed to human cells.

In particular, the present invention provides a fibroblast cell line comprising a monamine oxidase A gene comprising a mutation of at least one nucleotide. It is preferred that the fibroblast cell be a human fibroblast. Any of the cells of the invention may be immortalized or transformed to derive cell lines therefrom (see, for example, Yarder, F. et al., *J. Neurobiol.* 121(2):356–375 (1990); Evrard, C., *Proc. Natl. Acad. Sci. USA* 87:3062–3066 (1990); Bernard, O. et al., *J. Neurosci. Res.* 24:9–20 (1989); Moura Neto, V., *Develop. Brain Res.* 26:11–22 (1986); Graf, L. H. et al., *Somatic Cell Genet.* 5:1031–1044 (1979); Fulger, F. K. R. et al., *Molec. Cell Biol.* 2:1373–1387 (1982); Ingles, C. et al., *Molec. Cell Biol.* 2:666–673 (1982); Robson, C. N. et al., *Mutation Res.* 163:201–208 (1986)).

Cell lines provided in the present invention will be useful in the methods of the present invention. The cells will be of particular use in making normal and mutant monamine oxidase proteins which are useful in the enzymatic and immunological methods of the invention. Moreover, one skilled in the art will realize that the cells may be readily adapted to many methods known and employed in the art in order to further analyze the effects of monamine oxidase genes and proteins on cellular metabolism or determine the structure of the monamine oxidase molecule. For example, the cell lines provided in the present invention will be useful for the synthesis and subsequent extraction of monamine oxidase proteins. In this manner one skilled in the art can use these cells with large-scale tissue culture apparatus to achieve high yields of protein useful for many purposes (See, for example, Kaufman, R. J. High level production of proteins from mammalian cells, p. 155–198. In: *Genetic Engineering: Principles and Methods*, J. K. Setlow (Ed.) Plenum Press, New York (1987)), such as, for example, the formation of crystals for crystallographic studies (see, generally, Van Holde, *Physical Biochemistry*, Prentice-Hall, New Jersey (1972)) and the rational design of therapeutic agents.

III. Monamine Oxidase Proteins

The present invention further provides a substantially purified mutant monamine oxidase protein, particularly, but not limited to a monamine oxidase A protein (SEQ ID NO:32). It is preferred that the protein comprises an amino acid sequence encoded by a gene comprising a mutation in exon 8 (SEQ ID NO:33), and particularly, but not limited to, a C to T mutation in exon 8 at nucleotide 936 which creates an inframe termination codon. The present invention further provides a truncated protein about 296 amino acids in length.

It is contemplated by the present invention that one skilled in the art can target various regions of mutant monamine oxidase with various compounds which will bind or otherwise recognize the molecule. See generally, for example, Kaspczak et al., *Biochemistry* 28:9230–9238 (1989) and Harlow, *Antibodies*, Cold Spring Harbor Press, New York (1990) both of which are incorporated by reference herein. For instance, it is contemplated that a variety of truncated and mutant monamine oxidase proteins provided by the present invention will be useful in the production of antibodies that are specific to mutant monamine oxidase protein but not normal monamine oxidase protein. Those skilled in art will understand that certain truncated and mutant proteins have novel epitopes that are not present on normal proteins. Certain truncations and mutations of a protein will liberate epitopes which are buried in normal proteins, and will also create novel structures that are not present in the normal proteins. Skilled artisans will know how to make or select antibodies which recognize these novel epitopes using techniques known in the art. See, for example, Ausubel, F. M. et al., *Current Protocols in Molecular Biology*, published by Current Protocols, pp. 11.4.2–11.13.4 (1993); Harlowe, E. and Lane, D., *Antibodies a Laboratory Manual*, Cold Spring Harbor Laboratories (1988) both of which are incorporated by reference herein.

The term "antibody", as used herein, refers to both monoclonal antibodies which are a substantially homogenous population and to polyclonal antibodies which are heterogenous populations. Antibodies may be from any immunoglobulin class, including IgG, IgM, IgE, IgA, IgD and any subclass thereof. The term "antibody", as used herein, is also meant to include both natural intact molecules and fragments thereof, such as, for example, Fab and F(ab')$_2$, which are capable of binding antigen or hapten, as well as fusion constructs capable of binding antigen or hapten comprising immunoglobulin fragments and fragments of other molecules. The term "antibody" is also to be construed to include humanized antibodies of various other species as well as immunoglobulins or fusions therefrom expressed in a prokaryotic cell.

Both monoclonal and polyclonal antibodies to monamine oxidase will be made according to methods well known in the art. See, for example, Ausubel, F. M. et al., *Current Protocols in Molecular Biology*, published by Current Protocols, pp. 11.4.2–11.13.4 (1993). Hybridomas may be created using the cells of the present invention for the production of monoclonal antibodies. See, for example, Kohler et al., *Eur. J. Immuno.* 6:292 (1976). Antibodies may be generated against monamine oxidase protein produced recombinantly or isolated from cells and tissues where they naturally occur. Antibodies may also be generated against entire monamine oxidase protein or peptide subfragments therefrom comprising either domains of the protein, epitopes, or regions important to enzyme function.

It is contemplated by the present invention that substantially purified mutant monamine oxidase protein will be useful in immunoassays. One skilled in the art can readily use substantially purified protein of the invention as the starting point to develop immunoassays using methods known in the art, such as, for example, radioimmunoassays, sandwich assays and immunodiffusion assays. See, for example, Kohler et al., *Nature* 256:495 (1975); Kohler et al., *Eur. J. Immunol.* 6:511 (1976); Kohler et al., *Eur. J. Immunol.* 6:292 (1976); Hammerling et al., In *Monoclonal Antibodies and T-Cell Hybridomas*, pp. 563–681, Elsevier, N (1981); Sambrook et al., *Molecular Cloning—A Laboratory Manual*, (Second Edition), Cold Spring Harbor Labs (1989), especially Chapter 18 which outlines methods useful with substantially purified protein or antibodies raised to substantially purified protein. One method commonly known in the art is to make polyclonal or monoclonal antibodies to substantially purified proteins. See, for example, Harlowe, E. and Lane, D., *Antibodies a Laboratory Manual*, Cold Spring Harbor Laboratories, 1988.

The present invention contemplates raising antibodies against substantially purified mutant and normal monamine oxidase protein. It will be readily apparent to those skilled in the art how to use these antibodies in immunoassays for many purposes. For example, using the anti-monamine oxidase antibodies of the invention, one will be able to perform Western blot analyses of proteins in bodily fluids or tissue biopsies from individuals suspected of making mutant monamine oxidase in order to detect the presence mutant protein in a test sample. Skilled artisans will also be able use antimonamine oxidase antibody in in situ immunoassays to probe for the presence of mutant monamine oxidase in cultured or biopsied cells from individuals suspected of making mutant monamine oxidase. It is also contemplated that anti-monamine oxidase antibodies will be useful as immunoimaging reagents to directly image monamine oxidase and mutant monamine oxidase in the relevant tissues of an individual. It is further contemplated that anti-monamine oxidase antibodies will be useful as immunoaffinity reagents to enable skilled artisans to purify monamine oxidase protein from cultured cells and tissues of individuals. It is further contemplated by the invention to bind polyclonal serum or antibody to a support, then probe for the serum or antibody to the protein using labelled substantially purified protein. The invention also contemplates methods to probe bound antibody or serum with substantially purified protein and detect the binding using labelled antibodies raised against substantially purified protein. See, for example, Davis et al., *Microbiology: Including Immunology and Molecular Genetics*, Third Edition, Harper & Row, Philadelphia, 1980, particularly Ch. 16 and 17 for a description of antibodyantigen reactions and immunoglobulin molecules and genes which is incorporated by reference herein.

IV. Assays For Detection of Mutant Monamine Oxidase and Diagnosis of Associated Disorders A. Immunoassays As used herein, the term "bodily tissue" refers generally to all cells of an organism, particularly, but not limited to those cells which form complexes, networks, or lattices. The term "bodily tissue" is to be construed to include, but not be limited to, blood cells, skin cells, muscle cells, bone cells, and cells of the various organs.

The present invention provides methods for the detection of mutant monamine oxidase in bodily tissue comprising: obtaining a sample of bodily tissue suspected to contain mutant monamine oxidase; contacting the sample of bodily tissue with anti-mutant monamine oxidase antibody; and, detecting an anti-mutant monamine oxidase antibody-mutant monamine oxidase complex.

It is preferred that the methods comprise fibroblasts. It is also preferred that the antibody of the method is a monoclonal antibody. It is further preferred that the monamine oxidase of the method is monamine oxidase A, particularly, but not limited to human monamine oxidase A (SEQ ID NO:33).

Tissue suspected to contain mutant monamine oxidase may be isolated from an individual exhibiting an abnormal phenotype. The abnormal phenotype associated with monamine oxidase A deficiency may be manifested in a variety of behaviors, including, for example, aggression, proclivity to commit arson, proclivity to commit rape, exhibitionism, and altered patterns of REM sleep. The abnormal phenotype of affected individuals also includes hypersensitive crises in response to foods containing "false"amine transmitters.

Kits are provided which are useful with the methods of the present invention and comprise an anti-mutant monamine oxidase antibody, a labelled antibody capable of binding anti-mutant monamine oxidase antibody-monamine oxidase complex, and a solid support capable of binding protein.

It is preferred that the kits comprise a convenient plastic container for holding the various components. It is more preferred that the kits comprise a self-contained hand-held assay device whereby samples can be introduced, tested, results can be obtained, and the contaminated kit device can then be safely discarded. Those skilled in the art will recognize proper storage and stabilizing buffers for the reagents in the kits.

As used herein, the term "first anti-monamine oxidase antibody capable of binding mutant monamine oxidase" refers to antibody that recognizes at least one epitope on mutant monamine oxidase and is thereby capable of binding mutant monamine oxidase under conditions known by those in the art to be suitable for antigen-antibody binding. Normal monamine oxidase may also be recognized by this antibody if the recognized epitope or epitopes are shared with mutant monamine oxidase.

As used herein, the term "a second anti-monamine oxidase antibody incapable of binding mutant oxidase but capable of binding normal monamine oxidase" refers to antibody that does not recognize and will not bind mutant monamine oxidase but is capable of binding normal monamine oxidase since this antibody recognizes an epitope or epitopes which are not shared with mutant monamine oxidase.

As used herein, the terms "isolating" and "providing" generally refer to preparing a compound to be tested or analyzed in a manner suitable for the test or analysis, or preparing an extract containing a compound to analyzed or tested.

The present invention provides methods for the detection of mutant monamine oxidase in bodily tissue comprising: obtaining a sample of bodily tissue suspected to contain a mutant monamine oxidase gene; contacting the sample of bodily tissue with a first anti-monamine oxidase antibody capable of binding mutant monamine oxidase and a second anti-monamine oxidase antibody incapable of binding mutant oxidase but capable of binding normal monamine oxidase; and detecting a first anti-mutant monamine oxidase antibody-mutant monamine oxidase complex and the absence of a second anti-mutant monamine oxidase antibody-mutant monamine oxidase complex.

It is preferred in the method that the bodily tissue comprise fibroblasts, particularly, but not limited to human fibroblasts. It is also preferred that both the first antibody and the second antibody be a monoclonal antibody. A method is further provided wherein the monamine oxidase is monamine oxidase A.

Kits are provided which are useful with the methods of the present invention and comprise a first anti-monamine oxidase antibody, a second antimonamine oxidase antibody, a labelled antibody capable of binding a first and a second anti-monamine oxidase antibody-monamine oxidase complex, and a solid support capable of binding protein. One skilled in the art could readily adapt the kits of the present invention to methods devised using methods of the present invention as a starting point.

It is preferred that the kits be self-contained and hand-held as aforementioned.

Bodily tissue used in the methods of the invention can be obtained by any of the various techniques known and employed in the art, including, but not being limited to, punch biopsying, swabbing, tissue aspirating, lavaging, scraping and phlebotomizing. It is contemplated by the invention that the bodily tissue can be used directly for the extraction of protein or nucleic acid, or can be maintained in culture prior to such extractions. Cultured cells of the invention may comprise primary cells or immortalized cell lines. See, for example, Jat P. S. and Sharp, P. A., *J. Virol.* 59:746 (1986).

As used herein, "disease state" refers to that state of an individual which is phenotypically not normal as compared with phenotypically normal individuals and may be manifested by a homozygotic mutation or mutations of the monamine oxidase gene leading to reduced protein expression or production of a protein with lowered activity. The term "disease state" is also to be construed as encompassing behaviors such as aggression, proclivity to commit arson, proclivity to commit rape, and exhibitionism, and altered patterns of REM sleep. A carrier is not included among members exhibiting the diseased state.

B. Genetic Assays

Skilled artisans will recognize numerous applications for the genetic assays used in the detection of mutant monamine oxidase genes. Screening of individuals suspected of carrying a monamine oxidase gene mutation associated with abnormal behavior is but one important use. Such screening will be especially useful in genetic counselling, as well as for determining therapeutic approaches available to homozygotes. Such assays are also sorely needed to detect impulsive aggressive individuals who are not being treated or are otherwise disadvantaged by not being recognized as having a genetic disorder.

Accordingly, provided in the present invention are methods for determining whether an individual is a carrier of a mutant monamine oxidase gene or has a disease state associated with a mutant monamine oxidase gene comprising the steps of: selecting cells suspected of comprising a mutant monamine oxidase gene; providing nucleic acid from the cells; contacting the nucleic acid with at least one probe capable of detecting at least one mutation in the monamine oxidase gene; and detecting the presence of the mutation in at least one monamine oxidase gene.

A preferred embodiment is provided whereby the detecting step further comprises the steps of: counting the number of gene copies comprising the mutation detected; and determining if the number of the gene copies counted corresponds to a normal genotype, a mutant heterozygous genotype or a mutant homozygous genotype.

Skilled artisans can interpret the sequence data obtained using the present methods for detecting genetic mutations by direct comparison to the known sequence of the non-mutant monamine oxidase A gene. In this way, nonsense and missense mutations can be simply determined. Many techniques will be useful to map monamine oxidase mutations to enable skilled artisans to determine if an individual has a normal genotype, a mutant heterozygous genotype or a mutant homozygous genotype. For example, RFLP analyses can be used to determine which copy of the gene is being mapped. Moreover, for example, if two copies of a mutation associated impulsive aggression is detected, then the individual is a homozygous carrier. Further, for example, if one copy of a mutation associated impulsive aggression is detected, then the individual is an heterozygous affected individual.

Cells and bodily tissue used in the genetic methods of the invention can be obtained by of the aforementioned techniques known and employed in the art.

Preferred embodiments of the methods for determining whether an individual is a carrier of a mutant monamine oxidase gene or has a disease state associated with a mutant monamine oxidase gene comprise in the selecting step, blood cells, especially human blood cells.

A preferred embodiment of the contacting step of the above genetic methods further comprises the steps of: isolating RNA from the nucleic acid; contacting the RNA with at least one primer capable of priming cDNA synthesis; synthesizing first strand cDNA from the primers; contacting the cDNA with at least one primer capable of priming extension product synthesis; synthesizing primer extension products from the primers; and, amplifying the extension products using polymerase chain reaction to yield amplified nucleic acid.

Preferred genetic methods are provided for determining whether an individual is a carrier of a mutant monamine oxidase gene associated with impulsive aggression or has a disease state associated with a mutant monamine oxidase gene.

The present invention further provides RNA with at least one primer capable of priming cDNA synthesis; synthesizing first strand cDNA from the primers; contacting the cDNA with at least one primer capable of priming extension product synthesis; synthesizing primer extension products from the primers; and, amplifying the extension products using polymerase chain reaction to yield amplified nucleic acid; and detecting the presence of mutant nucleotides in the sequences isolated.

It is preferred that methods for determining the presence of a monamine oxidase gene defect in a cell from an individual suspected to contain a monamine oxidase gene mutation associated with abnormal behavior including impulsive aggression utilize single-strand conformational polymorphism (hereinafter "SSCP") PCR techniques. One skilled in the art will be able to readily adapt the methods of the invention to SSCP techniques to derive many useful techniques. SSCP techniques are described in, for example, Orita, M. et al., Proc. Natl. Acad. Sci. USA 86:2766–2770 (1989), which is incorporated herein by reference.

In a preferred embodiment of the methods for determining the presence of a monamine oxidase gene defect in a cell from an individual suspected to contain a monamine oxidase gene mutation associated with abnormal behavior including impulsive aggression the selecting step comprises blood cells, especially human blood cells.

RNA may be isolated by any of the many techniques known and used in the art. See, for example Chomczynski, P. et al., Anal. Biochem. 162:156 (1987). Moreover, skilled artisans will be able to readily develop alternative techniques for synthesizing and amplifying cDNA based on the methods of the invention.

Detection of a mutation in amplified cDNA can be conveniently analyzed by one of the many sequencing methods employed in the art. Sequencing may be carried out one or both of the cDNA strands. See, for example, van den Ouweland, A. M. W. et al., Nature Genetics 2:99 (1992).

Kits are provided comprising primers capable of priming first strand cDNA synthesis of a monamine oxidase A and gene primers capable of priming PCR. It is preferred that these kits be embodied in a plastic housing comprising vials of each reagent and a printed sequence of a non-mutant monamine oxidase A gene including variant non-mutant sequences.

It is preferred that the PCR methods of the invention use oligonucleotide primers capable of detecting a mutation in a monamine oxidase A gene. It is more preferred that such PCR methods use oligonucleotide primers capable of detecting a mutation in monamine oxidase A gene. It is most preferred that such PCR methods use oligonucleotide primers capable of detecting a mutation in a monamine oxidase A gene comprising sequences consisting essentially of a sequence selected from the group consisting of: AGT-TGATAGAAGGGTCCTTC (SEQ ID NO:1); CAGGC-CACTGCTACGGTCCACAC (SEQ ID NO:2); GGAAC-CAATTTTTCTCTTTT (SEQ ID NO:3); TCACTTGGGTGAAAAGTCAG (SEQ ID NO:4); TATGT-TCTAGGGGAAACA (SEQ ID NO:5); ACACATTTAC-CTCCTTCCC (SEQ ID NO:6); AGAGGTGGCAGTTAC-CATCA (SEQ ID NO:7); AATTTTGAATGGTCAAGTCT (SEQ ID NO:8); ATTGCAACAGAAAAACTT (SEQ ID NO:9); AGAAAGCAAAATCACAGA (SEQ ID NO:10); CTTTCTTACCTACCTCCTC (SEQ ID NO:11); ACTGAGTTACCTCATAATG (SEQ ID NO:12); GACTGCAGCTCACATCTGAGG (SEQ ID NO:13); ACCTCCTGTTCAATAATC (SEQ ID NO:14); CCCATTGATTTTTCTCCT (SEQ ID NO:15); ATGCAGAAGACCCTGTCTAAC (SEQ ID NO:16); ACAGCTGTAACCTGATCATTC (SEQ ID NO:17); AGCAAAATACAAAAGGTT (SEQ ID NO:18); TTTTTTTTTTGGCTCTGTT (SEQ ID NO: 19); TGCTTTGCTTTACTACTT (SEQ ID NO:20); TTTGTTAAAGCAACTATA (SEQ ID NO:21); AATTTGCACTGAACTCTG (SEQ ID NO:22); AGTCATACGGGTGTTTTT (SEQ ID NO:23); CCTTCCCGAGACCATTTA (SEQ ID NO:24); GAAAGCCCAGGCTCTCTC (SEQ ID NO:25); ATAGTGCCCAGAGTCACCAA (SEQ ID NO:26); GACGTTCCAGAGGTAGAAAT (SEQ ID NO:27); ACATGAGTGATCTACACTG (SEQ ID NO:28); CGACCTTGACTGCCAAGAT (SEQ ID NO:29); and CTTCTTCTTCCAGAAGGC (SEQ ID NO:30).

Methods of the present invention are useful to screen for carriers of monamine oxidase gene mutations associated with abnormal behaviors, especially impulsive aggression. This screening may be done as part of genetic counselling. Moreover, genetic assay methods are useful for prenatal screening and testing to determine if an embryo or fetus is homozygous or heterozygous for a mutant monamine oxidase gene, particularly mutations associated with impulsive aggression, and especially mutations in the monamine oxidase A gene (SEQ ID NO:31). Of particular use in prenatal screening are methods for determining the presence of a monamine oxidase gene mutation associated with a mutant monamine oxidase gene disease state. However, methods of the present invention can be easily adapted by skilled artisans to allow prenatal testing and screening using modified procedures. Moreover, one skilled in the art can readily isolate cells, tissues or bodily fluids useful for prenatal testing. For example, cells can be isolated from the chorionic villus, and cells, tissues or bodily fluids can be readily obtained by amniocentesis.

C. Assays to Detect Monamine Oxidase Deficiency

Assays to detect monamine oxidase deficiency in individuals exhibiting various abnormal behaviors, particularly impulsive aggression, are useful as a primary screening technique to determine if the abnormal behavior is genetically-based. Such screening will indicate to skilled artisans the need for further genetic characterization of individuals exhibiting abnormal behaviors. For example, if the methods of the invention indicate that the individual possesses a low monamine oxidase A level or activity, or abnormal amine metabolites in plasma, CSF or urine, and that individual also exhibits impulsive aggression or another behavior which is indicative of a genetically-based disorder, the individual should be further screened for a monamine oxidase A gene mutation. Monamine oxidase activity screening will also be useful to determine proper therapeutic approaches for impulsive aggressive individuals who are disadvantaged by not being recognized as having a genetic disorder.

As used herein, the term "compound capable of being modified by monamine oxidase" refers generally to any compound or analyte which, when introduced into the proximity of a sample comprising monamine oxidase or mutant monamine oxidase will be altered, such as by, for example, chemical modification or physical modification. As used herein, the term "modified" or "modification" refers generally to changes in the structure or function of the compound capable of being modified by mutant or normal monamine oxidase. The compound or analyte may undergo chemical modification, such as for example, addition of a novel moiety, deletion of a moiety, alteration of molecular configuration, or induction of dimerization or polymerization.

Accordingly, methods are provided for determining monamine oxidase deficiency in an individual exhibiting a disease state or behavior associated with a monamine oxidase gene mutation to diagnose a genetic basis for the disease state or behavior comprising the steps of: selecting cells from an individual suspected of having a monamine oxidase deficiency; culturing the cells isolated; preparing a homogenate from the cells cultured; contacting the homogenate with a compound capable of being modified by monamine oxidase; detecting the compound modified; comparing the compound modified by monamine oxidase from an individual suspected of having a monamine oxidase deficiency to control cells from a normal individual prepared by the method of the culturing step through the detecting step; and, determining if the individual suspected of having a monamine oxidase deficiency has the deficiency indicating a genetic basis for the behavior.

A preferred embodiment of the method comprises any treatment which can increase levels of normal protein. A more preferred embodiment of the method comprises a culturing step which comprises dexamethasone. Another preferred embodiment comprises contacting the homogenate with a compound capable of being modified by monamine oxidase A.

Further methods are provided for determining monamine oxidase A deficiency in an individual exhibiting a disease state or behavior associated with a monamine oxidase gene mutation to diagnose a genetic basis for the disease state or behavior comprising the steps of: selecting cells from an individual suspected of having a monamine oxidase A deficiency associated with abnormal behavior; and, determining if the individual suspected of having a monamine oxidase A deficiency has the deficiency indicating a genetic basis for the abnormal behavior.

In a preferred embodiment the selecting step further comprises the steps of: culturing the cells isolated; preparing a homogenate from the cells cultured; contacting the homogenate with a compound capable of being modified by monamine oxidase; detecting the compound modified; and, comparing the compound modified by monamine oxidase A from an individual suspected of having a monamine oxidase A deficiency to control cells from a normal individual prepared by the method of the culturing step through the detecting step to determine if the individual suspected of having a monamine oxidase A deficiency has the deficiency indicating a genetic basis for the behavior.

It is preferred that the methods to detect monamine oxidase deficiency be used to screen individuals exhibiting impulsive aggression to detect a genetic basis for the behavior.

One skilled in the art will recognize the utility of the methods of the invention to diagnose various disease states or behaviors associated with a monamine oxidase gene mutation to diagnose a genetic basis for the disease state or behavior. For example, individuals exhibiting impulsive aggression can be screened using the methods of the invention to determine if these individuals have lowered monamine oxidase A activity or lowered monamine oxidase A levels associated with a genetic basis for the abnormal behavior.

It is preferred that the methods to diagnose various disease states associated with monamine oxidase gene mutations be carried out in tandem with analysis of the individual's metabolite levels and direct genetic analyses, such as, for example measurement of 3-methoxy-4-hydroxyphenylglycol (hereinafter "MHPG") levels and genotyping respectively.

Various cell culturing methods known and employed by those skilled in the will be useful in the methods of the present invention. In certain embodiments of the invention it will be useful to create immortalized cell lines from individuals suspected of having a monamine oxidase deficiency, especially from individuals suspected to contain a monamine oxidase gene mutation associated with impulsive aggression. This may be done by introducing into the cells various genes useful for transformation and immortalization.

Cell homogenates in the present invention can be simply prepared using, for example, chemical cytolysis, biological cytolysis and physical cytolysis, including maceration, trituration, alkaline lysis, detergent lysis, osmotic lysis, freeze-thaw lysis, and sonication.

One skilled in the art will immediately recognize that compounds capable of being modified include, for example, natural and synthetic substrates of monamine oxidase, and compounds that can detect enzymatically altered substrates of monamine oxidase, such as anti-hapten antibodies.

The present invention also includes methods wherein the detecting step comprises various compounds, such as, for example, those capable of recognizing, binding to, or reacting to a compound capable of being modified by monamine oxidase. Antibodies and lectins are examples of such compounds.

The detecting step may comprise various compounds capable of being modified by monamine oxidase and which emit a signal that can be detected by, for example, photographic emulsion, radioactivity sensing equipment, NMR, CAT scanning and MRI.

It will be understood by skilled artisans that detection can be enhanced by labelling the compound capable of being modified by monamine oxidase. Labels useful in the methods of the present invention include, but are not limited to, flourescers, ligands, chromophores, chromogens, luminescers including chemoluminescers and bioluminescers, and radionuclides. One skilled in the art will immediately recognize that these labelling materials will also be useful to label the antibodies of the present invention, including, for example, the anti-monamine oxidase antibodies and antibodies that recognize anti-monamine oxidase antibody or anti-monamine oxidase antibody-monamine oxidase complexes.

The present invention further provides methods for determining monamine oxidase A deficiency in an individual exhibiting a disease state or behavior associated with a monamine oxidase gene mutation to diagnose a genetic basis for the disease state or behavior comprising the steps of: isolating bodily fluid or tissue from an individual suspected of having a monamine oxidase A deficiency; separating at least one metabolite component associated with a monamine oxidase A activity or level from the bodily fluid or tissue by size or quantity of each the component; detecting the size or quantity of each the metabolite component, comparing the size or quantity of each metabolite component from an individual suspected of having a monamine oxidase deficiency to the size or quantity of each metabolite component from a normal individual prepared by the method of the first isolating step through the detecting step; and, determining if the individual suspected of having a monamine oxidase A deficiency has a metabolite component of the size or quantity associated with a monamine oxidase A deficiency. A preferred method provides that in the separating step the separation by size or quantity be performed using mass fragmentography. It is most preferred that the metabolite detected be MHPG.

One skilled in the art will readily recognize that individuals exhibiting abnormal behavior including impulsive aggression can be screened using the methods of the present invention to determine if these individuals have metabolite levels indicative of lowered monamine oxidase A activity or lowered monamine oxidase A levels associated with a mutant monamine oxidase gene and abnormal behavior.

V. Non-Human Transgenic Animals

A. Non-Human Transgenic Animals Comprising Novel Sequence

According to the present invention mutant monamine oxidase genes are useful in making non-human transgenic animals to aid in the development of animal models of monamine oxidase deficiency. The present invention contemplates various non-human transgenic animals. Methods for making transgenic animals are commonly known and employed in the art. For example, see Palmiter et al., *Science* 222:809–814 (1983); Hammer et al., *Nature* 315:680–683 (1987); and, U.S. Pat. No. 5,175,385, all three of which are incorporated herein by reference.

Those skilled in the art commonly employ procedures for creating non-human transgenic animals through the introduction of a DNA molecule into the male pronucleus of a fertilized egg (Brinster, R. L. et al., *Cell* 27:223 (1981); Constantini, F. et al., *Nature* 294:92 (1981); Harbers, K., et al., *Nature* 293:540 (1981); Wagner, E. F. et al., *Proc. Natl. Acad. Sci. USA* 78:5016 (1981); Gordan, J. W., et al., *Proc. Natl. Acad. Sci. USA* 73:1260 (1976)).

One skilled in the art will be able to make numerous gene constructs comprising a monamine oxidase gene for use in non-human transgenic animals. It is further contemplated that vectors provided by the present invention will be useful in the production of non-human transgenic animals, however, it not necessary to use vectors to create non-human transgenic animals. See, for example, Jaenisch, R., *Science* 235:53 (1987); Hammer, R. E. et al., *Science* 235:53 (1987); Chada, K. et al., *Nature* 319:685 (1986), Kollias, G. et al., *Cell* 96:89 (1986); Shani, M., *Molec. Cell Biol.* 6:2624 (1986)).

By selective breeding of transgenic animals, it is possible to produce heterologous and homologous animals. Moreover, transgenic animals have been shown to be stable over generations and maintain and express the inserted gene.

Transgenic animals may be produced by recombinant viral and retroviral procedures in which the virus is used as a vector to introduce a sequence or gene of interest into the genome of the recipient cell. Retroviruses can be integrated into the host cell genome, usually as a single copy, and with little associated mutation (Janeisch, R., *Science* 240:1468 (1988)).

Accordingly, the present invention provides a transgenic animal substantially all of whose somatic and germ cells comprise and express a gene coding for monamine oxidase, the gene having been introduced into the animal or an ancestor of the animal at an embryonic stage. It is preferred that the transgenic animal's gene coding for monamine oxidase is a gene coding for mutant monamine oxidase A.

particularly, but not limited to a human gene. It is also preferred that transgenic animal be a mouse.

B. Non-Human Transgenic Animals Genetically Altered to Carry Mutant Monamine Oxidase Genes Chimerae can be produced using transgenic pluripotent embryonic stem cell (hereinafter "ES") techniques. These techniques utilize introduction of a DNA sequence of a gene into blastocyst from a developing embryo to create a chimeric animal (Robertson, E. et al., *Cold Spring Harbor Conf. Cell Prolif.* 10: 647–663 (1983); Bradley, A. et al., *Nature* 309:255 (1984); Wagner, E. F. et al., *Cold Spring Harbor Symp. Quant. Biol.* 50:691–700 (1985), all three of which references are incorporated herein by reference).

Techniques for producing chimeric animals may provide for ES cells to be cultured in vitro and infected with various vectors, including viral and retroviral vectors, comprising the gene or sequence of interest. Moreover, chimeric animals generated in this manner may have germ cells lacking the introduced sequence or gene. It has been further observed that the introduced gene or sequence may be present albeit unexpressed (Evens, M. J. et al., *Cold Spring Harbor Symp. Quant. Biol.* 50:685–689 (1985); Stewart, C. L. et al., *EMBO J.* 4:3701–3709 (1985), both of which are incorporated herein by reference).

One skilled in the art would understand that the ES cells may be selected for mutations in certain sequences or genes of interest (Hooper, M., *Nature* 326:295 (1987); Kuehn, M. R. et al., *Nature* 326:295 (1987)). Following such selection, one skilled in the art would also know that transgenic or chimeric non-human animals can be created that do not express the gene of interest, or which have a disabled sequence of interest as indicated by a gene under its control (Doetschman, T. et al., *Proc. Natl. Acad. Sci. USA* 85:8583 (1988); Gossler, A. et al., *Proc. Natl. Acad. Sci. USA* 83:9065 (1986); Takahashi, Y. et al., *Devel.* 102:258 (1988), all three of which are incorporated herein by reference).

Animal strains with defects in at least one monamine oxidase gene can be created through targeted gene disruption by homologous recombination into the monamine oxidase genes of ES cell lines followed by creation of chimeric embryos and subsequent breeding of chimeric animals (Rossant, J., *Neuron* 2:323–334 (1990); M. R. Capecchi, *Science* 244:1288–1292 (1989); K. R. Thomas and M. R. Capecchi, *Cell* 51:503–512 (1987), all three of which are incorporated herein by reference). This technique has been increasingly used in "knocking out" a variety of genes. For example, see S. Mansour et al., *Genet. Anal. Tech. Appl.* 7:219–227 (1990); A. L. Joyner et al., *Science* 251:1239–1243 (1991). Mice with specific gene lesions have also been created (M. Zijlstra et al., *Nature* 342:435–438 (1989); M. J. Grusby et al., *Science* 253:14717–1420 (1991)).

Monamine oxidase genes may be disrupted in ES cells by homologous replacement recombination using techniques known and used in the art (M. J. Grusby et al., *Science* 253:14717–1420 (1991). Constructs may be created to optimize targeted recombination (K. R. Thomas and M. R. Capecchi, *Cell* 51:503–512 (1987)).

Accordingly, the present invention provides a non-human transgenic animal of which has been genetically altered such that the animal has a monamine oxidase deficiency, particularly a monamine oxidase A deficiency. It is preferred that the deficiency be caused by a mutation in the monamine oxidase A coding sequence SEQ ID NO:31), and in particular by the introduction of a stop codon upstream of the normal stop codon, preferably in exon 8 SEQ ID NO:33). It is further preferred that the deficiency be caused by a genetic alteration which affects the level of expression of the monamine oxidase gene or the activity of the monamine oxidase protein expressed.

It is contemplated that DNA constructs will be made in which are useful for the creation of a "knock out" transgenic animal. One skilled in the art will realize that numerous constructs may be made for such use. For example, it is preferred that constructs be made in which exon 1 of the mouse monamine oxidase gene is disrupted by insertion of the selectable neo$^r$ gene and flanked by 10–15 kb of the corresponding mouse genomic sequence. Constructs may be with a selectable marker gene to allow for selection against non-homologous recombination events. One skilled in the will know appropriate markers for such use. For example, Herpes simplex virus thymidine kinase (HSV-TK) is a useful marker in the transgenic constructs of the invention. It is preferred that the HSV-TK gene, including its promoter, be ligated onto both ends of the construct (S. L. Mansour et al., *Nature* 336:348–352 (1988)).

A library comprising the genomic DNA of the species used for transgene incorporation will be screened to obtain a clone of the target monamine oxidase gene. Skilled artisans will realize that the insert obtained may be subcloned into a vector for ease of handling and mutation. For example, subcloning may be done in the pUC19 vector to facilitate sequencing across the site of mutation. This vector may also be used to prepare further constructs useful for homologous recombination into ES cells.

Skilled artisans will also understand that constructs may be linearized prior to transfection, and transfected by any of the numerous methods known in the art, such as electroporation. It is preferred that transfected ES cells be grown under selection, such as, for example, for neo$^r$ and against HSV-TK. Once established, cell clones will be expanded and tested for correct incorporation of the transgene. It is preferred that this be done by PCR amplification across inserted and endogenous sequences. Incorporation may also be examined by loss of monamine oxidase A activity. Once a monamine oxidase-deficient ES cell line is established, it will be microinjected into a mouse blastocyst to generate an ES cell-chimeric animal. It is preferred that this animal be a mouse.

It is also preferred that these chimeric animals be bred to establish heterozygous females and deficient males. It is contemplated that monamine oxidase-deficient animals will be characterized with respect to monamine oxidase activity, and neuronal development.

One skilled in the art will be able to use ES cell lines so they may be targeted and passed through a germ line (S. Mansour et al., *Genet. Anal. Tech. Appl.* 7:219–227 (1990); T. Doetschman et al., *Proc. Natl. Acad. Sci. USA* 85:8583–8587 (1988); M. J. Grusby et al., *Science* 253:14717–1420 (1991); M. Zijlstra et al., *Nature* 342:435–438 (1989), all four of which have been incorporated by reference herein).

Cells may be maintained and handled by any of the many methods known and used in the art. See, for example, E. J. Robertson, in *Teratocarcinomas and Embryonic Stem Cells: A Practical Approach*, E. J. Robertson, ed., Oxford IRL, 1987, pp. 71–112; R. Hogan et al., *Manipulating the Mouse Embryo*, Cold Spring Harbor Press, New York, 1986), both of which are incorporated herein by reference. It is preferred that cells be maintained on a feeder cell layer (E. J. Robertson, in *Teratocarcinomas and Embryonic Stem Cells:*

*A Practical Approach*, E. J. Robertson, ed., Oxford IRL, pp. 71–112 (1987)). It is further preferred that these cells may be cultured in specialized media comprising various growth factors. See, for example, S. Thompson et al., *Cell* 56:313–321 (1989). It is still further preferred that the ES cells be kept at low density to prevent undesirable effects on differentiation and karyotype.

Cells will be plated after transfection and viability will be determined. Cells will be placed under selection for the selectable marker utilized. It is preferred that at this time, the number of total recombinants and homologous recombinants will be assessed, and colonies will be picked and plated. Some cells from a colony will be used to detect if the mutation of interest is present. Methods of the present invention, as well as those known in the art, will be useful for this purpose. For example, PCR analysis may be utilized. It is preferred that primers be selected to span one recombinational junction, so that amplification will only be successful if homologous recombination has occurred. Colonies manifesting homologous recombination events will be expanded using techniques known in the art.

Targeted ES cells will be microinjected into blastocysts removed from pregnant females postcoitus. The injected blastocysts will then be surgically placed in the uterus of a pseudopregnant foster mother and allowed to develop to term. Chimeric offspring will be identified using techniques known in the art. Male chimerae will then be bred by females with offspring being derived from ES cells. DNA or RNA from cells or bodily fluids will be used to analyze the disrupted monamine oxidase gene in these offspring. Recombinant mice will be bred to achieve a new strain. These methods are described in detail in, for example, R. Hogan et al., *Manipulating the Mouse Embryo*, Cold Spring Harbor Press, New York, 1986; and, A. Bradley, in *Teratocarcinomas and Embryonic Stem Cells: A Practical Approach*, E. J. Robertson, ed., Oxford IRL, 1987, pp. 71–112, both of which are incorporated herein by reference.

VI. Vectors for Cloning and Expressing Monamine Oxidase Genes

The present invention provides numerous vectors comprising mutant monamine oxidase genes useful in various cells for cloning and subcloning of selected sequences as well as for expression of monamine oxidase protein. One skilled in the art will be readily able to make numerous gene constructs comprising monamine oxidase genes for use in prokaryotic and eukaryotic expression systems and for cloning. Skilled artisans will realize that eukaryotic cells particularly useful for expression of monamine oxidase include, but are not limited to, mammalian cells (Ramabdadran et al., *Gene* 38:111 (1985), and Wigler et al., *Cell* 16:777 (1979)), yeast cells (Valenzuala et al. *Nature* 298:347 (1982); Tuite et al., *EMBO J.* 1:603 (1982) and Smith et al., *Science* 229:1219 (1985)), insect cells, plant cells and avian cells (Highkin, M. K. et al., *Poultry Science* 70:970–981 (1991)). Chimeric viral vectors comprising a gene of the present invention will be useful for gene expression (Stephens, P. E. et al., *Biochem. J.* 248:1–11 (1987)). Chimeric constructs useful in eukaryotic gene expression comprising a monamine oxidase gene may further comprise heterologous gene expression control elements, such as, for example, promoters (Hamer, D. H. et al., *J. Molec. Appl. Gen.* 1:273–288 (1982)), hormone and toxin responsive elements (Danesch, U. et al., *EMBO J.* 6:625–630 (1987), and Campbell, M. E. M. et al., *J. Mol. Biol.* 180:1–19 (1984)), polyadenylation regions (Gimmi, E. R. et al., *Nucl. Acids Res.* 16 (18):8977–8997 (1988); Pfarr, D. S. et al., *DNA* 5(2):115–122 (1986); Cole, C. N. et al., *Mol. Cell. Biol.* 3(2):267–279 (February 1983)), terminators (Dressler, G. R. et al., *J. Virol.* 61(9):2770–2776 (September 1987)), introns (Ryu, W.-S. et al., *J. Virol.* 63(10):4386–4394 (October 1989); Neuberger, M. S. et al., *Nucl. Acids. Res.* 16 (14):6713–6724 (1988)), splice sites (Huang, M. T. F. et al., *Mol. Cell. Biol.* 10(4):1805–1810 (April 1990); van Doren, K. et al., *Mol. Cell. Biol.* 10(4):1769–1772 (April 1990); Green, M. R., *Ann. Rev. Genet.* 20:671–708 (1986)), transactivation responsive regions, and enhancers (Thompson, C. C. et al., *Trends In Genetics* 8:232–236 (1992)). Promoters useful in such chimeric constructs include promoters from, for example, cytomegalovirus, SV40 virus, and HIV. Hormone and toxin responsive elements useful in such chimeric constructs include the glucocorticoid responsive element and the metallothionein promotor. Polyadenylation regions useful in such chimeric constructs include regions from, for example, SV40 early and late, human collagen and polyoma. Terminators useful in chimeric constructs include those from, for example, gastrin gene and adenovirus Type 2 fiber gene. Introns useful in chimeric constructs include, for example, bGH introns and SV40 small t intron. Splice sites useful in chimeric constructs include, for example, the SV40 small t splice site. Transactivation responsive regions useful in chimeric constructs include, for example, HIV tat and HSV-1 VP16. Enhancers useful in chimeric constructs include those from, for example, immunoglobulin H-chain, SV40 and HIV.

Prokaryotic expression systems are well known and used in the art. For example, Sambrook et al., *Molecular Cloning—A Laboratory Manual*, (Second Edition), Cold Spring Harbor Labs (1989) teach well known methods for constructing and using cloning and expression vectors.

The present invention further provides a DNA molecule comprising a vector and a monamine oxidase gene comprising a mutation of at least one nucleotide. A preferred embodiment provides a DNA molecule comprising a vector and monamine oxidase A gene SEQ ID NO:31).

A more preferred embodiment provides a DNA molecule comprising a vector and a monamine oxidase A gene comprising a mutation in exon 8 SEQ ID NO:33), and particularly, but not limited to, a C to T mutation at nucleotide 936.

A DNA molecule is also provided comprising a vector and a monamine oxidase A gene encoding a truncated protein about 296 amino acids in length. Further provided is a DNA molecule comprising a vector and a monamine oxidase A gene comprising an in-frame termination codon upstream of the normal termination codon. The present invention further provides a DNA molecule comprising a vector and a monamine oxidase A gene encoding a monamine oxidase protein having lowered activity.

IV. Therapies For Monamine Oxidase Deficiency

It is contemplated that, in view of the discovery of specific mutations in the monamine oxidase A gene of individuals suffering from impulsive aggressive disorders, therapies can be developed to treat affected individuals.

Therapies to treat monamine oxidase A deficiency include providing individuals affected with normal monamine oxidase A genes or protein.

It is further contemplated that genes can be introduced into affected individuals using cells or vectors comprising the normal gene. Skilled artisans will recognize the appropriate bodily regions for the placement of cells useful to treat monamine oxidase deficiencies. Moreover, skilled artisans will be able to ascertain cell types useful for such therapies. It is contemplated that grafted cell expressing normal monamine oxidase will be useful as therapeutic agents.

Many methods of cell delivery are known in the art, such as, for example, implantation of membrane encapsulated cells. See U.S. Pat. Nos. 4,892,538; 5,011,472 and 5,106,627 each of which is incorporated herein by reference. Methods for cell encapsulation are further described in Aebischer et al., *Experimental Neurology* 111:269 (1991).

It is also contemplated that a normal gene or genes can be introduced into affected individuals using gene therapy strategies. Vectors, particularly viral vectors, comprising a normal gene will be useful for gene therapy. Genes and vectors can be delivered by many methods known in the art including, but not being limited to liposome delivery and viral transduction. Many other methods of gene delivery are known in the art.

It is still further contemplated that normal monamine oxidase protein will be useful to treat affected individuals. Protein can be introduced via many methods. These include, but are not limited to, liposome delivery, bolus delivery, or intravenous drip.

EXAMPLES

Example 1

Lowered Monamine Oxidase A Activity is Indicative of a Genetic Monamine Oxidase Mutation Introduction Urinary and plasma amines and amine metabolites were quantified in two individuals with Norrie disease resulting from a submicroscopic deletion in chromosomal region Xp11.3, recently reported to be associated with absence of the gene encoding monoamine oxidase and nondetectable monamine oxidase A activity in fibroblasts and monamine oxidase B activity in platelets. Marked reductions of 90% in levels of MHPG which is a deaminated metabolite of norepinephrine, a preferential substrate for monamine oxidase A in urine and plasma confirmed the presence of a systemic, functionally significant reduction in the activities of the monamine oxidase A isozyme.

In experiments described in this Example, the objective was to determine if patients had a mutation in a monamine oxidase A gene using metabolic profile screening assays.

Materials and Methods
Description of Patients

The subjects of this study (LGL515 and LGL541) were two male cousins, 12 and 16 years old, with Norrie disease (Norrie.G, Causes of blindness in children, *Acta Ophthamol.* (Copehn.) 5:357–386 (1927); Warburg, M., Norrie's disease: a congenital progressive occula-acoustica-cerebral degeneration, *Acta Ophthalmol.* (Copehn.) *Suppl.* 89:1–47 (1966); McKusick no. 31060) but with atypical features of the disease; they and two other affected males from one kinship were originally described as having a submicroscopic deletion, including the gene locus DXS7, on the short arm of the X chromosome, recognized by the anonymous probe LI.28 (de la Chappele et al., Norrie disease caused by a gene deletion allowing carrier detection and prenatal diagnosis, *Clin. Genet.* 28:317–320 (1985)). They had congenital blindness associated with retrolental masses and mental retardation typical of Norrie disease (Warburg, M., Norrie's disease: a congenital progressive occula-acoustica-cerebral degeneration, *Acta Ophthalmol.* (Copehn.) *Suppl.* 89:1–47 (1966)). Mental retardation was profound and progressive in these two patients. In addition, they had severe growth retardation and impaired sexual maturation; heights were 124 and 135 cm, and weights were 22.4 and 24.6 kg. Atonic seizures, myoclonic contractions, sleep disturbance, autistic-like social behavior, and peripheral autonomic dysfunction were also present (Sims, K. B. et al., *Neuron* 2:1069–1076 (1989)).

Plasma Samples

Plasma and platelet-rich plasma samples were collected using acid-citrate-dextrose solution as the anticoagulant (Murphy, D. L. et al., *Biochem. Med.* 16:254–265 (1976)). Duplicate 24 hour urine samples were collected under careful supervision on two separate days. The patients were receiving an institutional diet containing no caffeine. Plasma and urine samples from a 14-year-old healthy normal male (LGL2877) were collected and analyzed in parallel. All samples were stored at 70° C. until assayed. Samples were analyzed together with additional samples from nine age (15±2.4 years) and sex-matched healthy controls. Values obtained from these control subjects were very similar to those reported previously for other healthy controls studied in this laboratory.

Mass Fragmentography and HPLC

Urine samples were assayed by mass fragmentography, with the methodology summarized previously (Karoum, F. et al., in *Modern Methods in Pharmacology*, pp. 39–54 (Spector, S. and Back, N., eds.) Alan R. Liss, N.Y. (1982); Karoum, F., (*In Methods in Biogenic Amine Research*, (Parvez, S. et al. eds.) pp. 237–255, Elsevier Science Publ., Amsterdam (1983); and Karoum F., (In *Neuromethods*, Vol. 2, Baker, G. B. et al. eds.), pp. 305–325, Humana Press, Clifton, N.J. (1985)) and used in earlier and in ongoing studies of the effects of monamine oxidase inhibitors on urinary, CSF, and plasma amines and their metabolites (Karoum, F. et al., (*In Noncatecholic Phenylethylamines*, Part 2, (Mosnaim, A. D. et al., eds.) pp. 177–191, Marcek Dekker, New York (1980); Murphy,, D. L. et al., (*In Clinical Pharmacol. in Psychiatry: Neuroleptic and Antidepressant Res.*, (Usdin, E. et al. eds.), pp. 307–316 Macmillan, London (1981); Murphy, D. L. et al., (*In Neurobiol. of the Trace Amines*, (Boulton, A. A. et al., eds.) pp. 499–514, Humana Press, Clifton, N.J. (1984b); Karoum, F. et al., (*In Modern Methods in Pharmacology*, pp. 39–54 (Spector, S. and Back, N., eds.) Alan R. Liss, N.Y. (1982); Linnoila, M. et al., *Arch. Gen. Psychiatry* 39:513–516 (1982); Zametkin, A. et al., *Arch. Gen. Psychiatry* 42:969–973 (1985); Murphy et al., (manuscript in preparation)). All urinary data are reported in terms of units per gram of creatinine (mean±SD) to control for the smaller body mass resultant from the severe growth retardation in the patients. Urinary creatinine levels in the two patients were 374 and 520 mg/24 hours, compared with 1,244±569 mg/24 hours in the controls. Serotonin in platelet pellets and plasma MHPG were analyzed by HPLC, using electrochemical detection (Scheinin, M. et al., *Anal. Biochem.* 131:246–253 (1983); Tolliver, T. J. et al.,(Abstr.) *Soc. Neurosci. Abstr.* 14:212 (1988)). Analysis of urinary norepinephrine metabolites another report was performed using a different mass spectrometer and slightly different methodology (Sims, K. B. et al., *Neuron* 2:1069–1076 (1989)).

Results of Previous Analyses of Norrie Disease Patients Using Metabolite Assays

Compared with normal controls, the two Norrie disease deletion patients had markedly increased urinary excretion of trace amines.

Concentrations of the deaminated metabolites of norepinephrine, MHPG and vanillylmandelic acid (VMA), were markedly reduced in urine from the two patients, with values approximating only 10% of those of the controls (Table 2) (Murphy et al., *J. Neurochemistry* 54(1): 242 (1990)). Plasma MHPG content was below the level of reliable quantification (<0.3 ng/ml) compared with control values of 3.84±0.94 ng/ml (n=32). By contrast, excretion of the o-methylated catecholamine metabolites, normetanephrine and metanephrine (an epinephrine metabolite), was increased in these patients, whereas norepinephrine values were unchanged (Table 2). However, the summed urinary excretion of norepinephrine and its major metabolites, MHPG, VMA, and normetanephrine, was no different in the two patients (27.3 and 29.6 n mol/mg of creatinine) compared with the controls (29.8±5.7 n mol/mg of creatinine) (Murphy et al., *J. Neurochemistry* 54(1): 242 (1990)).

TABLE 2

Norepinephrine (NE) and catecholamine metabolites in 24-hour urine samples from Norrie disease deletion patients, a concurrently sampled age-matched control, and other sex- and age-matched controls (n = 9)

| Subjects | NE and catecholamine metabolites (mg/g of creatinine) | | | | |
|---|---|---|---|---|---|
| | MHPG | VMA | NMN | MN | NE |
| LGL515 | 0.14[a] | 0.44[a] | 4.11[a] | 0.29 | 0.45 |
| LGL541 | 0.13[a] | 0.35[a] | 3.87[a] | 0.39 | 0.69 |
| LGL2877 | 1.42 | 3.92 | 0.29 | 0.06 | 0.28 |
| Other controls | 1.31 ± 0.21 | 3.24 ± 0.91 | 0.39 ± 0.12 | 0.11± 0.06 | 0.27± 0.19 |

[a]Difference of >3 SD from the mean of the control group.
[b]Mean ± SD values.

Negligible differences in the deaminated metabolites of dopamine-3,4-dihydroxyphenylacetic acid (DOPAC) and homovanillic acid (HVA), or of dopamine itself were found in the patients compared with the controls (Table 3) (Murphy et al., *J. Neurochemistry* 54(1): 242 (1990)). However, concentrations of the o-methylated metabolite, 3-methoxytyramine, were increased approximately five-fold (Table 3). Platelet serotonin concentrations were somewhat higher in the patients (Table 4), whereas urinary 5-HIAA concentrations were within the range of values found for the controls (Table 4) (Murphy et al., *J. Neurochemistry* 54(1): 242 (1990)).

TABLE 3

Dopamine (DA) and its metabolites in 24-hour samples from Norrie disease deletion patients, a concurrently sampled age-matched control, and other sex- and age-matched controls (n = 9)

| Subjects | DA and metabolites (mg/g of creatinine) | | | |
|---|---|---|---|---|
| | DA | DOPAC | HVA | 3-methoxy-tyramine |
| LGL515 | 3.61 | 0.52 | 3.23 | 0.261[a] |
| LGL541 | 2.65 | 1.13 | 8.22 | 0.253[a] |
| LGL2877 | 2.32 | 0.94 | 4.22 | 0.04 |
| Other controls[b] | 0.70 ± 0.22 | 0.81 ± 0.55 | 5.74 ± 2.32 | 0.059 ± 0.015 |

[a]Difference of >3 SD from the mean of the control group.
[b]Mean ± SD values.

TABLE 4

Platelet serotonin and urinary 5-HIAA from Norrie disease deletion patients, a concurrently sampled age-matched control, and other sex- and age-matched controls (n = 9)

| Subjects | Platelet serotonin (ng/mg of protein) | Urinary 5-HIAA (mg/g of creatinine) |
|---|---|---|
| LGL515 | 0.82[a] | 3.07 |
| LGL541 | 1.01[a] | 1.64 |
| LGL2877 | 0.24 | 3.67 |
| Other controls[b] | 0.47 ± 0.10 | 1.99 ± 0.79 |

[a]Difference of >3 SD from the mean of the control group.
[b]Mean ± SD values.

It has been shown that marked reductions of about 90% in levels of urine and CSF MHPG comparable to those found in the Norrie disease deletion as aforementioned have been observed in humans and animals receiving a monamine oxidase A-selective inhibitor clorgyline (Murphy, D. L. et al., *J. Nerv. Ment. Dis.* 164:129–134 (1977); Major, L. R. et al., *J. Neurochem.* 32:229–231 (1979)); Pickar, D. et al., *Psychopharmacology (Berlin)* 74:8–12 (1981a); Pickar, D. et al., *Psychopharmacology (Berlin)* 74:4–7 1981b); Sunderland, T. et al., *Psychopharmacology (Berlin)* 86:432–437 (1985)). Patients receiving monamine oxidase inhibitors have changes in the amine and amine metabolite concentrations. (Pickar, D. et al., *Psychopharmacology (Berlin)* 74:8–12 (1981a); Pickar, D. et al., *Psychopharmacology (Berlin)* 74:4–7 (1981b); Sunderland, T. et al., *Psychopharmacology (Berlin)* 86:432–437 (1985)). Moreover, a close linear relationship has been shown between monamine oxidase A inhibition, as reflected in reduced plasma MHPG concentrations, and increased responsiveness to tyramine (Pickar, D. et al., *Psychopharmacology (Berlin)* 74:8–12 (1981a); Pickar, D. et al., *Psychopharmacology (Berlin)* 74:4–7 1981b); Sunderland, T. et al., *Psychopharmacology (Berlin)* 86:432–437 (1985)).

Results from Impulsive Aggressive Individuals

In view of the ability to ascertain monamine oxidase levels using certain metabolite profiles, metabolite analyses were carried out on the Dutch kindred and affected males exhibited reduced metabolite levels indicative of a monamine oxidase A deficiency. These individuals were further screened to determine their cellular monamine oxidase A activity and monamine oxidase A genotype as discussed hereinafter in Examples 2–4.

Example 2

Selective Monamine Oxidase A Deficiency in Humans Results in a Disturbance of Monamine Metabolism and is Associated with Abnormal Behavior Introduction In previous work, a large kindred was examined, in which several males are affected by a syndrome of borderline mental retardation and abnormal behavior, including disturbed regulation of impulsive aggression (Brunner, H. G. et al., *Am. J. Hum. Genet.* 52:1032 (1993)). The genetic defect for the impulsive aggressive condition was assigned to the p11-p21 region of the X chromosome, however, no gene responsible for the condition was identified. In other work, patients were evaluated for monamine oxidase deficiency, and monamine oxidase B activity was shown to be normal in affected males from this family (Brunner, H. G. et al., *Am. J. Hum. Genet.* 52:1032 (1993)) (FIG. 1).

In experiments described in this example, the objective was to determine if affected males in this family have selective monamine oxidase A deficiency.

Materials and Methods

Fibroblast Culture

Skin fibroblast cultures were established from three clinically affected males and from two carrier females. After informed consent was obtained, skin fibroblasts were established from punch biopsies of family members. Normal control cell lines were chosen on the basis of very low activity (GM2037), and moderately high activity (HF24) (Hotamisligil, G. S. et al., *Am. J. Hum. Genet.* 49:383 (1991)). All strains were in the proliferative stage of growth and were grown in parallel in DMEM with 10% fetal calf serum, penicillin and streptomycin (GIBCO, Paisley, Scotland).

Measurement of Monamine Oxidase Activity

Culture human skin fibroblasts express both monamine oxidase A and monamine oxidase B activity in a ratio of approximately 80-90% to 10-20%, respectively (Hotamisligil, G. S. et al., *Am. J. Hum. Genet.* 49:383 (1991)). Treatment of fibroblast cultures with dexamethasone produces a 6–14× increase in monamine oxidase A activity and a 2–3× increase in monamine oxidase B activity. Levels of activity are stable from passage to passage during the proliferative growth phase (Edelstein, S. B. et al., *Cell. Mol. Neuroblot.* 6:121 (1986)).

Monamine oxidase activity was assessed in homogenates from skin fibroblast strains using a common substrate, tryptamine, at a concentration which favors monamine oxidase A measurement. Monamine oxidase activity was measured using the toluene extraction procedure in fibroblast homogenates with 100 μg of protein per assay (Edelstein, S. B. et al., *Cell. Mol. Neuroblot.* 6:121 (1986)). All assays were performed in triplicate within the range of linearity for time. A buffer blank was used routinely, but in some cases additional blanks of $10^{-6}$M clorgyline (Sigma, St. Louis, Mo.) or $10^{-6}$M deprenyl were included. Thirty μM [ethyl-$^3$H]tryptamine (35 Ci/mmol., New England Nuclear, Boston, Mass.) was used as a common substrate for both monamine oxidase A and monamine oxidase B activity, although at this concentration monamine oxidase A is favored by its higher substrate affinity.

Strains from two normal controls were used which represent very low strain GM2037) and moderately high (strain HF24) levels of activity, based on previous analyses of over 30 control strains with activity levels spanning a range of 1 to 100 pmol/min/mg protein.

For measurement of monamine oxidase activity, cells were harvested at confluency (-dexamethasone) or after an additional 7–9 days of exposure to 50 nM dexamethasone (+dex), as described (Edelstein, S. B. et al., *J. Neurochem.* 31:1247 (1978)). Cell homogenates from two or more harvests were sonicated and protein determined by the method of Bradford (Bradford, M. M., *Anal. Biochem.* 72:248 (1976)); (Hotamisligil, G. S. et al., *Am. J. Hum. Genet.* 49:383 (1991)). These controls were grown in parallel with fibroblasts from family members to minimize activity differences due to serum components (Edelstein, S. B. et al., *Biochem. Biophys. Res. Commun.* 98:836 (1981)).

Results

Negligible levels of apparent monamine oxidase activity were found in strains from three affected males without or with dexamethasone treatment (Table 5). Levels of activity in two carrier females and in one non-carrier female from the same family were in the low to moderate control range and as in control strains were increased by treatment with dexamethasone and inhibited by over 90% the selective monamine oxidase A inhibitor, clorgyline (Table 5).

TABLE 5

| monamine oxidase activity in cultured skin fibroblasts | | |
|---|---|---|
| | −DEX | +DEX* |
| | (pmol/min/mg protein) | |
| Affected males: | | |
| BB | <1[+] | <1 |
| AW | <1 | <1 |
| AX | <1 | <1 |
| Carrier females: | | |
| AY | 10 ± 3 (n = 4)[++] | 114 ± 35 (n = 7) |
| AZ | 32 ± 9 (n = 4) | 122 ± 43 (n = 5) |
| Non-carrier female: | | |
| BA | 27 ± 16 (n = 4) | 189 ± (n = 5) |
| Normal controls: | | |
| GM2037 | 3 ± 3 (n = 4) | 24 ± 11 (n = 7) |
| HF24 | 36 ± 10 (n = 4) | 317 ± 42 (n = 5) |

*For the detection of monamine oxidase A activity, cells were harvested at confluency (DEX−) or after an additional 7-9 days of exposure to 50 nM dexamethasone (+DEX) as described (Edelstein, S. B. et al., J. Neurochem. 31:1247 (1978)).
[+]Activity levels were below detection limits and not inhibited by 1 μM clorgyline or deprenyl.
[++]All values are given as the average ± S.D. (n = number of assays).

Example 3

Lack of Monamine Oxidase A Activity is Caused by a Mutation in the Monamine Oxidase A Structural Gene.

Introduction

No previous studies have shown that a lack of monamine oxidase A activity is associated with abnormal behavior or caused by a mutation in the monamine oxidase A structural gene. The experiments disclosed in Examples 1 and 2 demonstrate that selective monamine oxidase A deficiency in humans results in a disturbance of monamine metabolism and is associated with abnormal behavior.

To demonstrate that the lack of monamine oxidase A activity was caused by a mutation in the monamine oxidase A structural gene, the coding sequence of the mRNA for monamine oxidase A was determined by first-strand cDNA synthesis, PCR amplification and direct sequencing.

Materials and Methods

RNA Isolation

RNA was isolated from fibroblasts by Acid Guanidinium Thiocyanate-Phenol-Chloroform extraction (Chomczynski, P. et al., *Anal. Biochem.* 162:156 (1987)) with a commercially available kit (Campro Scientific, Elst., The Netherlands)

First Strand cDNA Synthesis and Sequencing

First strand cDNA was synthesized from 2.5 micrograms of RNA with oligo dT and random primers with the Gene Amp kit (Perkin-Elmer, Branchburg, N.J.). Two overlapping fragments were prepared essentially as described previously (Hotamisligil, G. S. et al., *Am. J. Hum. Genet.* 49:383 (1991). Both strands from the 5'867 bp PCR fragment were sequenced as described (van den Ouweland, A. M. W. et al., *Nature Genetics* 2:99 (1992)), with the PCR primers and two internal primers, corresponding to nucleotide position 483–502 of the monamine oxidase A cDNA sequence (Hsu, Y.-P. P. et al., *Neurochemistry* 51:1321 (1988); Chen, Z.-Y. et al., *Nucl. Acids Res.* 19:4537 (1992)) in both directions. The 1010 bp 3' PCR fragment was sequenced with the PCR primers and four internal primers (np 1177-1206 in both 5'-3' and 3'-5' directions, np 1382-1401 (forward), np 1485-1505 (reverse). Sequence was determined on both strands except for the 300 3' bp of the 1010 bp PCR fragment.

Genomic DNA Amplification

Genomic DNA was amplified with primers corresponding to np 874-892 (forward: 5'-CGACCTTGACTGCCAAGAT-3')(SEQ ID NO:29) and 987-1004 (reverse: 5'-CTTCTTCTTCCAGAAGGC-3')(SEQ ID NO:30). To amplify the DNA, two-microliter aliquots of the first-strand cDNA products from 10 µg total fibroblast RNA or 500 mg genomic DNA were incorporated in 50 µl of a reaction mix containing 50 mM KCl, 10 mM Tris (pH 8.3), 1.5 mM $MgCl_3$, 100 µg gelatin/ml, 1 mM of each dNTP, 200 nM of each primer, and 2.5 U of Taq DNA polymerase (Perkin Elmer—Cetus). Thirty cycles of amplification (94° C. for 1 minute, 57° C. for 2 minutes, 72° C. for 3 minutes) were carried out with a final extension time of 10 minutes (Saiki et al. 1988). Three microliters of reaction mix was electrophoresed in a 1.1% agarose gel and was visualized by staining with ethidium bromide by using BstEII fragments of lambda DNA as size markers. The rest of the reaction mix was loaded on a 2% NuSieve GTG agarose (FMC, Bioproducts) in 1M Tris-borate/EDTA buffer (pH 8.0) and electrophoresed for 6 hours at 4.4 V/cm; the bands were excised from the gel or were eluted onto DEAE membranes (Schleicher & Schuell), as described (Fretzen et al. 1981), and were stored at –20° C. Following amplification, both strands were sequenced.

Linkage Analysis

Genetic linkage calculations were performed using the mlink program from the Linkage program package (version 5.03) (Lathrop, C. M. et al., *Am. J. Hum. Genet.* 36:460 (1984)).

Results

Four base substitutions were detected, three of which were neutral polymorphisms: G to T at position 941, a T to A at position 1077, and a T to C at position 1460. However, a non-conservative C to T mutation was found at position 936. This mutation changes a glutamine (CAG) codon to a termination (TAG) codon at position 296 of the deduced amino acid sequence (Hsu, Y.-P. P. et al., *Neurochemistry* 51:1321 (1988); Bach, A. W. J. et al., *Proc. Natl. Acad. Sci. USA* 85:4934 (1988); Chen, Z.-Y. et al., *Nucl. Acids Res.* 19:4537 (1992)). Amplification and sequencing of the 8th exon SEQ ID NO:33, which contains nucleotides 846 to 1005, confirmed the presence of the C to T mutation at nucleotide 936 in each of five clinically affected males, and in two obligatory heterozygotes (FIG. 1). In contrast, the mutation could be excluded in 12 unaffected males in this family (FIG. 1). Two-point linkage calculations were performed using the mlink program from the Linkage program package (version 5.03) (Lathrop, C. M. et al., *Am. J. Hum. Genet.* 36:460 (1984)). The two-point linkage calculations between the clinical phenotype and the mutation in the mutant monamine oxidase A gene yield a lod score of 3.55 without recombination.

These studies represent the first documentation of complete and selective deficiency of monamine oxidase A in affected males. Interestingly, the monamine oxidase A activity in two carrier females was not different from that of a non-carrier and from two unrelated controls.

Selective monamine oxidase A deficiency in this family results in a marked disturbance of monoamine metabolism. Raised urinary excretion of normetanephrine and tyramine, and decreased levels of 5-hydroxy-indole-3-acetic acid (5-HIAA), homovanillic acid (HVA), and vanillylmandelic acid (VMA) have been documented by analysis of 24-hour urine samples (Brunner, H. G. et al., *Am. J. Hum. Genet.* 52:1032 (1993)). The urinary findings reflect altered central neurotransmitter metabolism. Selective inhibition of monamine oxidase A in male rats has been shown to increase brain levels of noradrenaline, dopamine and serotonin (Sleight, A. J. et al., *Br. J. Pharmacol.* 93:303 (1988); Blier, P. et al., *J. Pharmacol. Exp. Therapeut.* 237:987 (1986); Greenshaw, A. J. et al., *Biol. Psychiatry* 25:1014 (1989); and Morden, B. et al., *Physiol. Behav.* 3:425 (1968)).

Five patients with X chromosomal deletions including both monamine oxidase A and monamine oxidase B as well as the Norrie disease gene have been described that had severe mental retardation (de la Chappelle, A. et al., *Clin. Genet.* 28:317; Bleeker-Wagemakers, E. M. et al., *Ophthalmic Paedlatr. Genet.* 9:137; Donnai, D. et al., *J. Med. Genet.* 25:73; Zhu, D. et al., *Sam. J. Med. Genet.* 33:485; and Collins, F. C. et al., *Am. J. Med. Genet.* 42:127 (1992)). The relatively mild symptoms in males with selective monamine oxidase A deficiency, and the absence of psychiatric symptoms or mental retardation in two brothers with a complex deletion involving the Norrie disease gene and part of the monamine oxidase B structural gene, leaving monamine oxidase A intact, (Berger, W. et al., *Nature Genet.* 1:199 (1992)) may reflect the overlapping substrate specificities and tissue distribution of the monamine oxidase A and monamine oxidase B isozymes.

The behavioral phenotype in this family is characterized by borderline mental retardation and a tendency towards aggressive outbursts, often in response to anger, fear, or frustration. These behavioral responses have been noted in each of eight affected males for whom clinical data are available, and have occurred in affected subjects living in different parts of the country at different times (Brunner, H. G. et al., *Am. J. Hum. Genet.* 52:1032 (1993)). It should be stressed that the aggressive behavior varied markedly in severity even within this single pedigree. Other types of impulsive behavior that occurred in individual cases included arson, attempted rape, and exhibitionism.

It has been postulated that aggression in animals can be subdivided into several subtypes (Valzelli, L., *Pharmacol. Res. Commun.* 14:1 (1982); Valzelli, L., Psychobiology of Aggression and Violence, Raven Press, New York, (1981)). In humans, impulsive aggression rather than premeditated aggression and violence has been linked to low levels of 5-HIAA in cerebrospinal fluid (Cocarro, E. F., *Br. J. Psychiatry* 155 (*Suppl.* 8):52 (1989)). This observation is usually taken to indicate a reduction in central serotonergic function in impulsive aggression. These data indicate that reduced 5-HIAA levels may also be caused by absent or reduced monamine oxidase A activity in these subjects. Monamine oxidase inhibition has not been reported to cause aggressive behavior in adult humans (de la Chappelle, A. et al., *Clin. Genet.* 28:317; Bleeker-Wagemakers, E. M. et al., *Ophthalmic Paedlatr. Genet.* 9:137; Donnai, D. et al., *J. Med. Genet.* 25:73; Zhu, D. et al., *Sam. J. Med. Genet.* 33:485; and Collins, F. C. et al., *Am. J. Med. Genet.* 42:127 (1992)), but deficiencies throughout life might have different consequences. Only limited data are available on monamine oxidase activity and aggression in regulation in animals. Monamine oxidase inhibition increased shock-induced aggression in male rats in one study (Eichelman, B. et al., *Pharmac. Biochem. Behav.* 3:601 (1975)). Other studies of aggressive behavior have stressed the importance of reduced serotonergic transmission (Valzelli, L., *Pharmacol. Res. Commun.* 14:1 (1982); Valzelli, L., Psychobiology of Aggression and Violence, Raven Press, New York, (1981); Cocarro, E. F., *Br. J. Psychiatry* 155 (Suppl. 8):52 (1989); Higley, J. D. et al., *Arch. Gen. Psychiatry* 49:436 (1992); Troncone, L. R. P. et al., *Physiol. Behav.* 50:173 (1991); Brown, G. L. et al., *Psychiatry Res.* 1:131 (1979); Linnoila, M. et al., *Life Sci.* 33:2609 (9183); Kantak, K. M. et al., *Pharmacol. Biochem. Behavior* 12:173 (1980); Kruesi, M. J. P. et al., *Arch. Gen. Psychiatry* 47:419 (1990); Popova, N. K. et al., *Aggress. Behav.* 17:207 (1991)), of increased dopaminergic transmission (Troncone, L. R. P. et al., *Physiol. Behav.* 50:173 (1991); Nikulina, E. M. et al., *Aggress. Behav.* 18:65 (1992); Tufik, S. et al., *Pharmacol.* 16:98 (1978)), or of increased noradrenergic transmission (Higley, J. D. et al., *Arch. Gen. Psychiatry* 49:436 (1992); Troncone, L. R. P. et al., *Physiol. Behav.* 50:173 (1991); Brown, G. L. et al., *Psychiatry Res.* 1:131 (1979); Eichelman, B. et al., *Biol. Psychiatry* 6:143 (1973); Winslow, J. T. et al., *Psychopharmacol.* 81:286 (1983)) in animals as well as in humans. Another factor that could be involved in causing increased impulsive aggression is rapid eye movement (REM) sleep deprivation. Monamine oxidase A inhibitors have been shown to suppress REM sleep in human subjects (Cohen, R. M. et al., *Psychopharmacol.* 78:137 (1982)), while REM sleep deprivation increases shock-induced fighting in rats, especially in combination with dopaminergic stimulation (Tufik, S. et al., *Pharmacol.* 16:98 (1978)). Monamine oxidase deficiency can also cause hypertensive crises in affected individuals.

Taken together, data obtained in this family show a relationship between isolated complete deficiency of monamine oxidase A activity and abnormal aggressive behavior in affected males.

Example 4

Immunological Detection of Mutant Monamine Oxidase in an Individual

Introduction

In order to simply screen individuals suspected to have a mutation in the monamine oxidase A gene associated with abnormal behavior including impulsive aggression, immunoassays will be developed.

Materials and Methods

Two samples of skin fibroblasts are obtained from a patient the cells of whom are suspected to contain mutant monamine oxidase. Cells in the samples are lysed and each lysed sample is adsorbed onto two separate regions of a solid substrate. The sample is then contacted with an anti-monamine oxidase antibody capable of binding mutant monamine oxidase and an anti-monamine oxidase antibody incapable of binding mutant oxidase but capable of binding normal monamine oxidase bound to a support under conditions suitable for binding. Samples are then washed with buffer to remove excess unbound antibody and tissue material. Antibody-antigen complex is then detected by contacting each sample with a labelled anti-heavy chain antibody.

Results

Results showing an anti-mutant monamine oxidase antibody-mutant monamine oxidase complex and the absence of an anti-mutant monamine oxidase antibody-mutant monamine oxidase complex indicate the presence of mutant monamine oxidase protein in the individual cells. If both complexes are detected, then normal monamine oxidase protein is present in the sample.

Example 5

Rapid PCR-Based Method for Screening the Human Monamine Oxidase A Gene For Exonic Mutations

Introduction

The experiments in Examples 1–4 demonstrate that there is a mutation in the monamine oxidase A gene (SEQ ID NO:31) which is associated with abnormal behaviors, including impulsive aggression. In order to facilitate simple screening for the genetic defect, a novel rapid screening process to detect single base changes, insertions, and deletions within the coding sequence of the human monamine oxidase A gene has been devised. This method utilizes primers in the flanking intron sequences of each of the fifteen monamine oxidase A exons (Table 1, SEQ ID NO:1 through SEQ ID NO:28). These primers are combined in sets and used in a small number of multiplex PCR reactions. The products of these reactions are used to detect mutations using SSCP analysis. Samples showing SSCP shifts are sequenced using direct sequencing. This method is exceedingly useful to screen DNA from males with features of the monamine oxidase A deficiency syndrome, as well as controls with very low enzyme activity as measured in cultured skin fibroblasts.

TABLE 1

Monamine Oxidase A Primers

| Exon | 5' Primer | Location | 3' Primer | Location | Fragment Size |
|---|---|---|---|---|---|
| 1 | AGTTGATAGAAGGGTCCTTC SEQ ID NO: 1 | (−)5 to 15 | CAGGCCACTGCTACGGTCCACAC SEQ ID NO: 2 | 146 + 1 to 146 + 27 | 178 |
| 3 | GGAACCAATTTTTCTCTTTT SEQ ID NO: 3 | 242-25 to 242-6 | TCACTTGGGTGAAAAGTCAG SEQ ID NO: 4 | 379 + 7 to 379 + 26 | 188 |
| 4 | TATGTTCTAGGGGAAACA SEQ ID NO: 5 | 380-10 to 387 | ACACATTTACCTCCTTCCC SEQ ID NO: 6 | 476 to 484 + 10 | 124 |
| 5 | AGAGGTGGCAGTTACCATCA SEQ ID NO: 7 | 485-40 to 485-31 | AATTTTGAATGGTCAAGTCT SEQ ID NO: 8 | 576 + 7 to 576 + 26 | 157 |
| 6 | ATTGCAACAGAAAAACTT SEQ ID NO: 9 | 577-111 to 577-94 | AGAAAGCAAAATCACAGA SEQ ID NO: 10 | 718 + 40 to 718 + 57 | 309 |
| 7 | CTTTCTTACCTACCTCCTC | 719-25 to 719-7 | ACTGAGTTACCTCATAATG | 860 to 868 + 10 | 184 |

TABLE 1-continued

Monamine Oxidase A Primers

| Exon | 5' Primer | Location | 3' Primer | Location | Fragment Size |
|---|---|---|---|---|---|
| | SEQ ID NO: 11 | | SEQ ID NO: 12 | | |
| 8 | GACTGCAGCTCACATCTGAGG | 869-47 to 869-27 | ACCTCCTGTTCAATAATC | 1028 + 59 to 1028 + 76 | 282 |
| | SEQ ID NO: 13 | | SEQ ID NO: 14 | | |
| 9 | CCCATTGATTTTTCTCCT | 1029-25 to 1029-8 | ATGCAGAAGACCCTGTCTAAC | 1125 + 5 to 1125 + 25 | 146 |
| | SEQ ID NO: 15 | | SEQ ID NO: 16 | | |
| 10 | ACAGCTGTAACCTGATCATTC | 1126-41 to 1126-21 | AGCAAAATACAAAAGGTT | 1179 + 127 to 1179 + 144 | 238 |
| | SEQ ID NO: 17 | | SEQ ID NO: 18 | | |
| 11 | TTTTTTTTTTGGCTCTGTT | 1180-25 to 1180-7 | TGCTTTGCTTTACTACTT | 1237 + 51 to 1237 + 68 | 150 |
| | SEQ ID NO: 19 | | SEQ ID NO: 20 | | |
| 12 | TTTGTTAAAGCAACTATA | 1238-82 to 1238-65 | AATTTGCACTGAACTCTG | 1335 + 58 to 1335 + 78 | 255 |
| | SEQ ID NO: 21 | | SEQ ID NO: 22 | | |
| 13 | AGTCATACGGGTGTTTTT | 1336-130 to 1336-113 | CCTTCCCGAGACCATTTA | 1552 to 1569 | 315 |
| | SEQ ID NO: 23 | | SEQ ID NO: 24 | | |
| 14 | GAAAGCCCAGGCTCTCTC | 1448-44 to 1448-27 | ATAGTGCCCAGAGTCACCAA | 1510 + 7 to 1510 + 26 | 132 |
| | SEQ ID NO: 25 | | SEQ ID NO: 26 | | |
| 15 | GACGTTCCAGAGGTAGAAAT | 1511 to 1530 | ACATGAGTGATCTACACTG | 1862 to 1880 | 369 |
| | SEQ ID NO: 27 | | SEQ ID NO: 28 | | |

Materials and Methods

Primers

For the monamine oxidase gene, primers in the flanking intronic or untranslated regions have been designed to amplify the coding regions of exons. This requires 14 primer pairs. Primers have been prepared which allow for the detection of mutations in each exon of the monamine oxidase A gene (Table 1, SEQ ID NO:1 through SEQ ID NO:28). The coding regions of the 15 exons range from 54 to 150 bp, and the thirteenth and fourteenth exon can be amplified together in a fragment of 225 bp. The primers are resolvable on a 1.4% agarose gel. Using a 1.4% agarose gel, bands can be resolved which differ in size by 20 bp in the 70 to 150 bp range and by 50 bp in the 150 to 300 bp range. Primer sets can be combined to increase the efficiency of the screen. The development of conditions for this multiplex PCR can be done by sequential addition and testing of primer pairs in a single reaction to achieve equal amplification of all fragments (Gibbs, R. A. et al., *Genomics* 7:235–244 (1990), which is incorporated herein by reference). Optimization can be readily achieved through adjusting the concentration of each primer set, evaluating different annealing and extension times and temperatures, and testing different primer pairs for the same exon. Once conditions are worked out, amplified fragments will be resolved on gels by SSCP (Orita, M. et al., *Proc. Natl. Acad. Sci. USA* 86:2766–2770 (1989), which is incorporated herein by reference).

Blood Sampling

Blood samples (10–20 ml) are obtained by routine venipuncture from male volunteers using acid citrate-dextrose tubes. Genomic DNA is extracted from blood samples by a standard SDS-proteinase K procedure involving phenol-chloroform extraction and ethanol precipitation (Breakefield, X. O. et al., *Science* 192:1018–1020 (1976), which is incorporated herein by reference). A typical yield is 200 µg DNA/10 ml blood sample.

DNA Amplification

Nanogram quantities of DNA may amplified using 18–20 nucleotide primers complementary to intronic sequence on either side of exons and at least 15 bp away from exon/intron junctions, as well as overlapping regions of the untranslated sequences. A standard amplification procedure involves a 50 µl reaction mix containing 50 mM KCl, 10 mM Tris (pH 8.3), 1.5 mM $MgCl_2$, 100 µg gelatin/ml, 1 mM each dNTP, 200 nM of each primer and 21.5 U Taq DNA polymerase (PerkinElmer Cetus) or Pyrococcus polymerase (Stratagene) using HPLC-grade water. Thirty cycles of amplification (94 C for 21 minutes, 55 C. for 1 minute, 72 C. for 1 minute) are carried out with a final extension of time for 10 minutes, as based on Saiki, R. K. et al., *Science* 239:487–491 (1988), which is incorporated herein by reference. Ten µl of the reaction mix are electrophoresed in a 1.5% agarose gel and visualized by staining with ethidium bromide using PvuII fragments of lambda DNA as size markers. Conditions will be established to achieve abundant amplification of a single fragment of the appropriate size. The $MgCl_2$ concentration and annealing temperature and time may be further optimized for particular sets of primers.

SSCP Analysis

For SSCP analysis, PCR products are internally labeled by direct incorporation of [alpha-$^{32}$P]dGTP (0.2 mM, 3000 Ci/mmole, NEN) during the amplification reaction. Aliquotes are diluted into a 50% formamide solution in water containing dye markers, bromophenol blue and xylene cyanol. DNA is denatured by heating at 95 C. for 5 minutes and samples loaded immediately onto a 5% acrylamide/10% glycerol gels. Nondenatured DNA samples of several reactions are loaded in separate lanes to determine their migration. Electrophoresis is carried out at room temperature at 20 mA or less overnight, taking care that the gel does not become too warm. In some cases one may use the MDE gel system (AT Biochemicals) and electrophoresis at 4 C. to help resolve fragments. Gels are dried and exposed to X-ray film for 1–3 days. All fragments with altered migration are sequenced as well as all fragments from individuals with dramatically altered levels of metabolites.

One efficient way to sequence these fragments is to carry out asymmetric PCR (see, for example, Innes et al., 1988) followed by direct sequencing (Gorman, K. B. et al., *Biotechniques* 7:326–329 (1989)). First, an unlabeled DNA fragment (150 to 250 bp) will be amplified under standard conditions and evaluated by gel electrophoresis, as described elsewhere herein. A small aliquot of the initial reaction will then be amplified under the same conditions using only one of the primers and a portion again checked by gel electrophoresis for purity. This sample will then be "cleaned" by several precipitations in ammonium acetate and ethanol and resuspended in TE buffer. This DNA will be denatured at 95° C. for 3 minutes and then annealed to the other primer at 65° C. for 5 minutes. Sequencing by dideoxy chain termination (Sanger, F. et al., *Proc. Natl. Acad. Sci. USA* 74:5463–5468 (1988)) will then be carried out using modified T7 polymerase (Sequenase, USB) in the presence of containing 7M urea. Each fragment will be sequenced over its entirety in both directions by reversing the order of use of primers.

Results

Sequence variations observed in the monamine oxidase A exons will be sequenced for all coding regions of that allele. Additional blood samples will also be obtained from other members of the same family to evaluate the inheritance of the mutant allele. Exons 11, 12 and 13 are highly conserved among all monamine oxidase cDNAs characterized to date. Moreover, it has been reported that exon 12 encodes the cysteine residue used for covalent attachment of the FAD cofactor (Chen, Z.-Y. et al., *Nucl. Acids. Res.* 19:4537–4541 (1991); Grimsby, J. et al., *Proc. Natl. Acad. Sci. USA* 88::3637–3641 (1991)) and hence represents part of the active site of the enzyme. Any bp mutation in these three codons which alters the type of amino acid at a given position would likely disrupt enzyme activity. In other cases it may be difficult to interpret the possible consequences of certain missense mutations in the gene on enzyme activity. Skin biopsies from at least one male bearing should be obtained for each type of mutation in order to culture the cells and measure monamine oxidase A activity directly.

Example 6

Transgenic Mice Genetically Altered to Carry Mutant Monamine Oxidase Genes

Introduction

One certain way to understand the developmental and functional consequences of monamine oxidase deficiency is to create mice strains with defects in either or both of these genes. This can be done through targeted gene disruption by homologous recombination into the monamine oxidase genes of cultured embryonic stem (ES) cell lines followed by creation of chimeric embryos and subsequent breeding of chimeric animals (M. R. Capecchi, *Science* 244:1288–1292 (1989); K. R. Thomas and M. R. Capecchi, *Cell* 51:503–512 (1987)). This technique has been increasingly used in "knocking out" a variety of genes (e.g., S. Mansour et al., *Genet. Anal. Tech. Appl.* 7:219–227 (1990); A. L. Joyner et al., *Science* 251:1239–1243 (1991)).

Transgenic mice overexpressing monamine oxidase B have been created. Mice with other specific gene lesions have also been reported (M. Zijlstra et al., *Nature* 342:435–438 (1989); M. J. Grusby et al., *Science* 253:14717–1420 (1991)).

To further understand the affects of monamine oxidase deficiency, the present experiments are directed to the creation of an animal model. To this end, ES cell lines exhibiting high monamine oxidase activity have been developed. This high level of expression and the fact that there is a single monamine oxidase gene in males should make the creation of a "knock-out" straightforward.

Materials and Methods
Experimental Outline

DNA constructs will be created in which exon 1 of the mouse MIA gene is disrupted by insertion of the selectable neo$^r$ gene and flanked by 10–15 kb of the corresponding mouse genomic sequence. Constructs will be flanked with genes for Herpes simplex virus thymidine kinase (HSV-TK) to allow for selection against non-homologous recombination events. Constructs will be linearized and transfected by electroporation into ES cells. Cells will be grown under selection for neo$^r$ and against HSV-TK. Cell clones will be expanded and tested for correct incorporation of the transgene by PCR amplification across inserted and endogenous sequences and by loss of monamine oxidase A activity. When an monamine oxidase A-deficient ES cell line is established, it will be microinjected into a mouse blastocyst to generate ES cell-chimeric mice. These mice will be bred to establish heterozygous females and deficient males. Monamine oxidase A-deficient animals will be characterized with respect to monamine oxidase activity, neuronal development, and behavior.

Constructs

Mouse monamine oxidase genes in ES cells will be disrupted by homologous replacement recombination with plasmid constructs bearing the first exon of these genes disrupted by insertion of neo$^r$ gene, as described (M. J. Grusby et al., *Science* 253:14717–1420 (1991). Constructs will contain 10–15 kb of homologous sequences around the first exon to optimize targeted recombination (K. R. Thomas and M. R. Capecchi, *Cell* 51:503–512 (1987)). The HSV-TK gene, including its promoter, will be ligated onto both ends of the construct to allow selection against non-homologous recombination events (S. L. Mansour et al., *Nature* 336:348–352 (1988)). The monamine oxidase A gene will be targeted first, as it is expressed earlier than the monamine oxidase B gene in development.

An EMBL Cos library of the mouse genome is screened for the appropriate clone. A clone obtained containing a 15 kb insert which includes the first exon of monamine oxidase A bearing the ATG start site of translation and a putative FAD non-covalent binding domain will be used in these experiments (W. Weyler et al., in Flavins and Flavoproteins, Walter de Guyter, New York, 1987, pp. 725–739). This insert has been reclined into the pUC19 vector and sequenced across the first exon. This plasmid will be digested with TthIII to remove a 50 bp section from the coding region of exon 1, including the putative FAD non-covalent binding domain. This section will then be replaced with the pMC1neo-polyA expression unit (Stratagene) which contains a tandem repeat of the polyoma mutant pYF441 enhancer element, the HSV-TK promoter, a synthetic translation initiation sequence, and a polyA addition site. This construct will likely be effective in homologous recombination into ES cells. If the construct is not effective, other promoter elements driving neor introduced at other exons will be tested. Additional genomic fragments of the mouse monamine oxidase A gene and fragments of the monamine oxidase B gene will be isolated from the EMBL Cos library by screening with labelled probes representing different portions of the human cDNAs under varying conditions of stringency by standard procedures. See, for example, J. Sambrook et al., *Molecular Cloning*, Cold Spring Harbor Press, New York, 1989. Assuming that the exon 1 construct for monamine oxidase A, as described, will be effective, a similar construct will be prepared to disrupt the monamine oxidase B gene.

Embryonic Stem Cells

Four different mouse ES cell lines have been targeted and passed through a germ line (S. Mansour et al., *Genet. Anal. Tech. Appl.* 7:219–227 (1990)). Early passages of one of these lines, D3 (T. Doetschman et al., *Proc. Natl. Acad. Sci. USA* 85:8583–8587 (1988)), derived from male cells, have been obtained and used in successful targeting (M. J. Grusby et al., *Science* 253:14717–1420 (1991); M. Zijlstra et al.,

*Nature* 342:435–438 (1989)). In the present experiments these cells have been maintained at low density in DMEM with 20% fetal cell serum on a feeder layer of irradiated STO cells (E. J. Robertson, in *Teratocarcinomas and Embryonic Stem Cells: A Practical Approach*, E. J. Robertson, ed., Oxford IRL, pp. 71–112 (1987)). These cells will be cultured on gelatinized dishes in medium supplemented with recombinant leukemia inhibitory factor (LIF; ESGRO, Amrad) (S. Thompson et al., *Cell* 56:313–321 (1989)). Techniques for handling ES cells have been well described. See, for example, E. J. Robertson, in *Teratocarcinomas and Embryonic Stem Cells: A Practical Approach*, E. J. Robertson, ed., Oxford IRL, 1987, pp. 71–112; R. Hogan et al., *Manipulating the Mouse Embryo*, Cold Spring Harbor Press, New York, 1986), both of which are incorporated herein by reference. It is important to keep the ES cells at low density to present their differentiation and to passage them as few times as possible to maintain an euploid karyotype. Differentiation will be monitored by visual inspection, and the karyotype will be evaluated. It is likely that derivatives of the ES cell line will be successful in entering the germ line, however, other available lines will be tried (S. Mansour et al., *Genet. Anal. Tech. Appl.* 7:219–227 (1990)).

To achieve homologous recombination, 25 μg NotI-linearized plasmid DNA will be transfected into $10^7$ ES cells in suspension by electroporation at 240 V, 500 uF using a BIO-RAD Gene Pulser. Cells will be plated after transfection, as above, and viability will be determined. After 20 hrs cells will be placed under selection for neo alone (200 μg/ml G418, GIBCO) and in the presence of selection against the HSV-TK gene (3 μM ganciclovir, Syntex) for 9 days. At this time, the number of total recombinants (G418 alone) and homologous recombinants (G418 plus ganciclovir) will be assessed. This ratio varies from 1/100 to 1,1000 in experienced laboratories. Conditions of electroporation and drug concentrations will be optimized for survival of recombinant cells. Colonies will be picked and plated in microtiter plates, keeping out a portion of cells for mini-DNA extraction and PCR analysis. Primers will be selected to span one recombinational junction, with one in the neo' gene and one in endogenous sequences not more than 2 kb away, such that amplification will only be successful if homologous recombination has occurred. PCR amplification and gel analysis of fragments will be carried out as described elsewhere herein. Colonies manifesting homologous recombination events will be expanded to a limited degree to obtain DNA for Southern blot analysis to confirm a single and accurate site of insertion. A portion of these clones will also be grown to evaluate monamine oxidase A activity. Methods for measuring this activity are described elsewhere herein.

Embryonic manipulations

Ten to fifteen targeted ES cells will be microinjected into blastocysts removed from pregnant C57Bl/6 females at 3.5 days postcoitus. The injected blastocysts will then be surgically placed in the uterus of a pseudopregnant foster mother and allowed to develop to term. Chimeric offspring will be identified by a dominant agouti coat color gene from the ES cells. Male chimeras will then be bred by C57Bl/6 females with agouti offspring being derived from ES cells. DNA from tail clippings will be used to analyze the disrupted monamine oxidase gene in these offspring. Recombinant mice will be bred to achieve a new strains.

Chimeric Embryos

Mice of strain C57bl/6 and SW will be used to create and foster chimeric embryos. Chimeric mice will be bred and offspring analyzed for the transgene by PCR amplification of DNA, obtained from tail clippings. Transgenic animals will be sacrificed for determination of monamine oxidase activity levels in various tissue as well as for neuroanatomical analyses.

For these experiments adult C57Bl/6 females and foster Swiss Webster (SW) females will be obtained. The C57Bl/6 females will be used as a source of timed embryos for chimeric production. The SW females will be used as pseudopregnant mothers to carry embryos to term. Superovulation will be used rather than natural matings to reduce the size of the colony needed.

Embryo collection

Donor females will be superovulated with pregnant mare's serum followed 48 hrs later by human chorionic gonadotropin, then mated and checked for plugs. Fertilized animals will be sacrificed 3.5 days later by cervical dislocation. Blastocyst embryos will be removed by finishing uterine horns and microinjected with ES cells.

Survival surgery

Chimeric blastocysts will be implanted into the uterine horns of pseudopregnant SW mice, mated 2.5 days previously to vasectomized males. Embryo transfers will be performed under 15 cc/kg body weight Avertin anesthesia. No preoperative food withholding or special care is needed. The surgical approach is from a dorsal midline incision and small (5 mm) incision in the body wall. The ovary, oviduct and uterus are externalized briefly, the embryos transferred and the tissue returned to the body cavity. The peritoneum is sutured and the skin closed with surgical clips; the area will be monitored for infections or incomplete wound-closure. Animals will be monitored daily. If after the 20th day of gestation the surrogate mother has not delivered a litter, she will be sacrificed by cervical dislocation, and her pups taken by C-section and fostered on a lactating female. Vasectomies are performed on Adult SW males under Avertin delivered interperitoneally.

Tail biopsies will be routinely performed on all potential transgenic pups. The procedure will be done at weaning. The animals will be anesthetized briefly with halothane and 1.5 cm of the tail removed. Bleeding will be stopped by cauterization. Under these conditions, the animals show no signs or pain or distress. Any animals in distress following surgery will be euthanized by methods condoned by the Panel on Euthanasia of the American Veterinary Medical Association and then examined pathologically.

Histology and enzyme analysis

For histochemical analyses, mice will be deeply anesthetized and perfused transcardially with fixative. For biochemical analysis, they will be sacrificed by cervical dislocation.

Analysis of Transgenic Mouse Metabolism

Monamine oxidase A activity in tissues from these recombinant male mice will be examined. Gross aspects of neuronal development and, in particular, the effects of this deficiency on numbers and morphology of catecholaminergic and serotonergic neurons will also be examined. Amine metabolites in these animals will be analyzed, and kinetics of azmine receptors in the brain will be evaluated, as well as behavioral abnormalities.

What is claimed is:

1. A substantially purified monamine oxidase A gene having a mutation in exon 8 (SEQ ID NO:33) of at least one nucleotide, wherein said gene is a native genomic DNA segment or a cDNA copy of a native cellular RNA transcript and said mutation is a nonsense mutation or a naturally-occurring missense mutation and specifies a monamine oxidase product having decreased activity.

2. The monamine oxidase A gene of claim 1 wherein said mutation comprises a C to T mutation at nucleotide 936.

3. The monamine oxidase A gene of claim 1 wherein said gene is associated with abnormal behavior in an individual.

4. The monamine oxidase A gene of claim 1 wherein said mutation is a nonsense mutation.

5. The monamine oxidase A gene of claim 1 wherein said mutation is a naturally-occurring missense mutation.

6. A recombinant DNA molecule comprising a vector and a monamine oxidase A gene having a mutation of at least one nucleotide in the region corresponding to exon 8 (SEQ ID NO:33) of a native monamine oxidase A gene, wherein said mutation is a nonsense mutation or a naturally-occurring missense mutation and specifies a monamine oxidase product having decreased activity.

7. The DNA molecule of claim 6 wherein said monamine oxidase A gene comprises a C to T mutation at nucleotide 936.

8. The recombinant DNA molecule of claim 6 wherein said mutation is a nonsense mutation.

9. The recombinant DNA molecule of claim 6 wherein said mutation is a naturally-occurring missense mutation.

10. A cell line comprising a monamine oxidase A gene having a mutation of at least one nucleotide in the region corresponding to exon 8 (SEQ ID NO:33) of a native monamine oxidase A gene, wherein said mutation is a nonsense mutation or a naturally-occurring missense mutation and specifies a monamine oxidase product having decreased activity.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGTTGATAGA AGGGTCCTTC　　　　　　　　　　　　　　　　　　　　　　　　　　　　20

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CAGGCCACTG CTACGGTCCA CAC　　　　　　　　　　　　　　　　　　　　　　　　23

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGAACCAATT TTTCTCTTTT　　　　　　　　　　　　　　　　　　　　　　　　　　　　20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCACTTGGGT GAAAAGTCAG　　　　　　　　　　　　　　　　　　　　　　　　　　　　20

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TATGTTCTAG GGGAAACA　　　　　　　　　　　　　　　　　　　　　　　　　　　　　18

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ACACATTTAC CTCCTTCCC                                                                                    19

( 2 ) INFORMATION FOR SEQ ID NO:7:

( i ) SEQUENCE CHARACTERISTICS:
　　　　　　　　( A ) LENGTH: 20 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:7:

AGAGGTGGCA GTTACCATCA                                                                                   20

( 2 ) INFORMATION FOR SEQ ID NO:8:

( i ) SEQUENCE CHARACTERISTICS:
　　　　　　　　( A ) LENGTH: 20 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:8:

AATTTTGAAT GGTCAAGTCT                                                                                   20

( 2 ) INFORMATION FOR SEQ ID NO:9:

( i ) SEQUENCE CHARACTERISTICS:
　　　　　　　　( A ) LENGTH: 18 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:9:

ATTGCAACAG AAAAACTT                                                                                     18

( 2 ) INFORMATION FOR SEQ ID NO:10:

( i ) SEQUENCE CHARACTERISTICS:
　　　　　　　　( A ) LENGTH: 18 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:10:

AGAAAGCAAA ATCACAGA                                                                                     18

( 2 ) INFORMATION FOR SEQ ID NO:11:

( i ) SEQUENCE CHARACTERISTICS:
　　　　　　　　( A ) LENGTH: 19 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:11:

CTTTCTTACC TACCTCCTC                                                                                    19

( 2 ) INFORMATION FOR SEQ ID NO:12:

( i ) SEQUENCE CHARACTERISTICS:
　　　　　　　　( A ) LENGTH: 19 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:12:

```
ACTGAGTTAC CTCATAATG                                                                        19
```

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
GACTGCAGCT CACATCTGAG G                                                                     21
```

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
ACCTCCTGTT CAATAATC                                                                         18
```

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
CCCATTGATT TTTCTCCT                                                                         18
```

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
ATGCAGAAGA CCCTGTCTAA C                                                                     21
```

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
ACAGCTGTAA CCTGATCATT C                                                                     21
```

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
AGCAAAATAC AAAAGGTT                                                                         18
```

( 2 ) INFORMATION FOR SEQ ID NO:19:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

TTTTTTTTT GGCTCTGTT         19

( 2 ) INFORMATION FOR SEQ ID NO:20:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

TGCTTTGCTT TACTACTT         18

( 2 ) INFORMATION FOR SEQ ID NO:21:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

TTTGTTAAAG CAACTATA         18

( 2 ) INFORMATION FOR SEQ ID NO:22:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

AATTTGCACT GAACTCTG         18

( 2 ) INFORMATION FOR SEQ ID NO:23:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

AGTCATACGG GTGTTTTT         18

( 2 ) INFORMATION FOR SEQ ID NO:24:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

CCTTCCCGAG ACCATTTA         18

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GAAAGCCCAG GCTCTCTC                                  18

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

ATAGTGCCCA GAGTCACCAA                                20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GACGTTCCAG AGGTAGAAAT                                20

( 2 ) INFORMATION FOR SEQ ID NO:28:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

ACATGAGTGA TCTACACTG                                 19

( 2 ) INFORMATION FOR SEQ ID NO:29:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

CGACCTTGAC TGCCAAGAT                                 19

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CTTCTTCTTC CAGAAGGC                                  18

( 2 ) INFORMATION FOR SEQ ID NO:31:

( i ) SEQUENCE CHARACTERISTICS:
   ( A ) LENGTH: 1964 base pairs
   ( B ) TYPE: nucleic acid
   ( C ) STRANDEDNESS: both
   ( D ) TOPOLOGY: both ( i i ) MOLECULE TYPE: cDNA ( i x ) FEATURE:
   ( A ) NAME/KEY: CDS
   ( B ) LOCATION: 51..1631

( x i ) SEQUENCE DESCRIPTION: SEQ ID NO:31:

```
GAATTCCTGA CACGCTCCTG GGTCGTAGGC ACAGGAGTGG GGGCCAAAGC ATG GAG                 56
                                                         Met Glu
                                                         1

AAT CAA GAG AAG GCG AGT ATC GCG GGC CAC ATG TTC GAC GTA GTC GTG              104
Asn Gln Glu Lys Ala Ser Ile Ala Gly His Met Phe Asp Val Val Val
        5               10                  15

ATC GGA GGT GGC ATT TCA GGA CTA TCT GCT GCC AAA CTC TTG ACT GAA              152
Ile Gly Gly Gly Ile Ser Gly Leu Ser Ala Ala Lys Leu Leu Thr Glu
        20              25                  30

TAT GGC GTT AGT GTT TTG GTT TTA GAA GCT CGG GAC AGG GTT GGA GGA              200
Tyr Gly Val Ser Val Leu Val Leu Glu Ala Arg Asp Arg Val Gly Gly
35              40                  45                  50

AGA ACA TAT ACT ATA AGG AAT GAG CAT GTT GAT TAC GTA GAT GTT GGT              248
Arg Thr Tyr Thr Ile Arg Asn Glu His Val Asp Tyr Val Asp Val Gly
                55                  60                  65

GGA GCT TAT GTG GGA CCA ACC CAA AAC AGA ATC TTA CGC TTG TCT AAG              296
Gly Ala Tyr Val Gly Pro Thr Gln Asn Arg Ile Leu Arg Leu Ser Lys
            70                  75                  80

GAG CTG GGC ATA GAG ACT TAC AAA GTG AAT GTC AGT GAG CGT CTC GTT              344
Glu Leu Gly Ile Glu Thr Tyr Lys Val Asn Val Ser Glu Arg Leu Val
                85                  90                  95

CAA TAT GTC AAG GGG AAA ACA TAT CCA TTT CGG GGC GCC TTT CCA CCA              392
Gln Tyr Val Lys Gly Lys Thr Tyr Pro Phe Arg Gly Ala Phe Pro Pro
        100                 105                 110

GTA TGG AAT CCC ATT GCA TAT TTG GAT TAC AAT AAT CTG TGG AGG ACA              440
Val Trp Asn Pro Ile Ala Tyr Leu Asp Tyr Asn Asn Leu Trp Arg Thr
115                 120                 125                 130

ATA GAT AAC ATG GGG AAG GAG ATT CCA ACT GAT GCA CCC TGG GAG GCT              488
Ile Asp Asn Met Gly Lys Glu Ile Pro Thr Asp Ala Pro Trp Glu Ala
                135                 140                 145

CAA CAT GCT GAC AAA TGG GAC AAA ATG ACC ATG AAA GAG CTC ATT GAC              536
Gln His Ala Asp Lys Trp Asp Lys Met Thr Met Lys Glu Leu Ile Asp
            150                 155                 160

AAA ATC TGC TGG ACA AAG ACT GCT AGG CGG TTT GCT TAT CTT TTT GTG              584
Lys Ile Cys Trp Thr Lys Thr Ala Arg Arg Phe Ala Tyr Leu Phe Val
        165                 170                 175

AAT ATC AAT GTG ACC TCT GAG CCT CAC GAA GTG TCT GCC CTG TGG TTC              632
Asn Ile Asn Val Thr Ser Glu Pro His Glu Val Ser Ala Leu Trp Phe
        180                 185                 190

TTG TGG TAT GTG AAG CAG TGC GGG GGC ACC ACT CGG ATA TTC TCT GTC              680
Leu Trp Tyr Val Lys Gln Cys Gly Gly Thr Thr Arg Ile Phe Ser Val
195                 200                 205                 210

ACC AAT GGT GGC CAG GAA CGG AAG TTT GTA GGT GGA TCT GGT CAA GTG              728
Thr Asn Gly Gly Gln Glu Arg Lys Phe Val Gly Gly Ser Gly Gln Val
            215                 220                 225

AGC GAA CGG ATA ATG GAC CTC CTC GGA GAC CAA GTG AAG CTG AAC CAT              776
Ser Glu Arg Ile Met Asp Leu Leu Gly Asp Gln Val Lys Leu Asn His
                230                 235                 240

CCT GTC ACT CAC GTT GAC CAG TCA AGT GAC AAC ATC ATC ATA GAG ACG              824
Pro Val Thr His Val Asp Gln Ser Ser Asp Asn Ile Ile Ile Glu Thr
```

-continued

```
              245                         250                         255
CTG AAC CAT GAA CAT TAT GAG TGC AAA TAC GTA ATT AAT GCG ATC CCT           872
Leu Asn His Glu His Tyr Glu Cys Lys Tyr Val Ile Asn Ala Ile Pro
    260             265                 270

CCG ACC TTG ACT GCC AAG ATT CAC TTC AGA CCA GAG CTT CCA GCA GAG           920
Pro Thr Leu Thr Ala Lys Ile His Phe Arg Pro Glu Leu Pro Ala Glu
275             280                 285                         290

AGA AAC CAG TTA ATT CAG CGT CTT CCA ATG GGA GCT GTC ATT AAG TGC           968
Arg Asn Gln Leu Ile Gln Arg Leu Pro Met Gly Ala Val Ile Lys Cys
                295                 300                 305

ATG ATG TAT TAC AAG GAG GCC TTC TGG AAG AAG AAG GAT TAC TGT GGC          1016
Met Met Tyr Tyr Lys Glu Ala Phe Trp Lys Lys Lys Asp Tyr Cys Gly
            310                 315                 320

TGC ATG ATC ATT GAA GAT GAA GAT GCT CCA ATT TCA ATA ACC TTG GAT          1064
Cys Met Ile Ile Glu Asp Glu Asp Ala Pro Ile Ser Ile Thr Leu Asp
        325                 330                 335

GAC ACC AAG CCA GAT GGG TCA CTG CCT GCC ATC ATG GGC TTC ATT CTT          1112
Asp Thr Lys Pro Asp Gly Ser Leu Pro Ala Ile Met Gly Phe Ile Leu
    340                 345                 350

GCC CGG AAA GCT GAT CGA CTT GCT AAG CTA CAT AAG GAA ATA AGG AAG          1160
Ala Arg Lys Ala Asp Arg Leu Ala Lys Leu His Lys Glu Ile Arg Lys
355                 360                 365                 370

AAG AAA ATC TGT GAG CTC TAT GCC AAA GTG CTG GGA TCC CAA GAA GCT          1208
Lys Lys Ile Cys Glu Leu Tyr Ala Lys Val Leu Gly Ser Gln Glu Ala
                375                 380                 385

TTA CAT CCA GTG CAT TAT GAA GAG AAG AAC TGG TGT GAG GAG CAG TAC          1256
Leu His Pro Val His Tyr Glu Glu Lys Asn Trp Cys Glu Glu Gln Tyr
            390                 395                 400

TCT GGG GGC TGC TAC ACG GCC TAC TTC CCT CCT GGG ATC ATG ACT CAA          1304
Ser Gly Gly Cys Tyr Thr Ala Tyr Phe Pro Pro Gly Ile Met Thr Gln
        405                 410                 415

TAT GGA AGG GTG ATT CGT CAA CCC GTG GGC AGG ATT TTC TTT GCG GGC          1352
Tyr Gly Arg Val Ile Arg Gln Pro Val Gly Arg Ile Phe Phe Ala Gly
    420                 425                 430

ACA GAG ACT GCC ACA AAG TGG AGC GGC TAC ATG GAA GGG GCA GTT GAG          1400
Thr Glu Thr Ala Thr Lys Trp Ser Gly Tyr Met Glu Gly Ala Val Glu
435                 440                 445                 450

GCT GGA GAA CGA GCA GCT AGG GAG GTC TTA AAT GGT CTC GGG AAG GTG          1448
Ala Gly Glu Arg Ala Ala Arg Glu Val Leu Asn Gly Leu Gly Lys Val
                455                 460                 465

ACC GAG AAA GAC ATC TGG GTA CAA GAA CCT GAA TCA AAG GAC GTT CCA          1496
Thr Glu Lys Asp Ile Trp Val Gln Glu Pro Glu Ser Lys Asp Val Pro
            470                 475                 480

GCG GTA GAA ATC ACC CAC ACC TTC TGG GAA AGG AAC CTG CCC TCT GTT          1544
Ala Val Glu Ile Thr His Thr Phe Trp Glu Arg Asn Leu Pro Ser Val
        485                 490                 495

TCT GGC CTG CTG AAG ATC ATT GGA TTT TCC ACA TCA GTA ACT GCC CTG          1592
Ser Gly Leu Leu Lys Ile Ile Gly Phe Ser Thr Ser Val Thr Ala Leu
    500                 505                 510

GGG TTT GTG CTG TAC AAA TAC AAG CTC CTG CCA CGG TCT TGAAGTTCTG           1641
Gly Phe Val Leu Tyr Lys Tyr Lys Leu Leu Pro Arg Ser
515                 520                 525

TTCTTATGCT CTCTGCTCAC TGGTTTTCAA TACCACCAAG AGGAAAATAT TGACAAGTTT        1701

AAAGGCTGTG TCATTGGGCC ATGTTTAAGT GTACTGGATT TAACTACCTT TGGCTTAATT        1761

CCAATCATTG TTAAAGTAAA AACAATTCAA AGAATCACCT AATTAATTTC AGTAAGATCA        1821

AGCTCCATCT TATTTGTCAG TGTAGATCAA CTCATGTTAA TTGATAGAAT AAAGCCTTGT        1881

GATCACTTTC TGAAATTCAC AAAGTTAAAC GTGATGTGCT CATCAGAAAC AAAAAAAAAA        1941
```

AAAAAAAAAA AAAAAAGGAA TTC       1964

( 2 ) INFORMATION FOR SEQ ID NO:32:

( i ) SEQUENCE CHARACTERISTICS:
        ( A ) LENGTH: 527 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Met Glu Asn Gln Glu Lys Ala Ser Ile Ala Gly His Met Phe Asp Val
 1               5                  10                  15

Val Val Ile Gly Gly Gly Ile Ser Gly Leu Ser Ala Ala Lys Leu Leu
                20                  25                  30

Thr Glu Tyr Gly Val Ser Val Leu Val Leu Glu Ala Arg Asp Arg Val
            35                  40                  45

Gly Gly Arg Thr Tyr Thr Ile Arg Asn Glu His Val Asp Tyr Val Asp
        50                  55                  60

Val Gly Gly Ala Tyr Val Gly Pro Thr Gln Asn Arg Ile Leu Arg Leu
 65                  70                  75                  80

Ser Lys Glu Leu Gly Ile Glu Thr Tyr Lys Val Asn Val Ser Glu Arg
                85                  90                  95

Leu Val Gln Tyr Val Lys Gly Lys Thr Tyr Pro Phe Arg Gly Ala Phe
               100                 105                 110

Pro Pro Val Trp Asn Pro Ile Ala Tyr Leu Asp Tyr Asn Asn Leu Trp
           115                 120                 125

Arg Thr Ile Asp Asn Met Gly Lys Glu Ile Pro Thr Asp Ala Pro Trp
       130                 135                 140

Glu Ala Gln His Ala Asp Lys Trp Asp Lys Met Thr Met Lys Glu Leu
145                 150                 155                 160

Ile Asp Lys Ile Cys Trp Thr Lys Thr Ala Arg Arg Phe Ala Tyr Leu
                165                 170                 175

Phe Val Asn Ile Asn Val Thr Ser Glu Pro His Glu Val Ser Ala Leu
           180                 185                 190

Trp Phe Leu Trp Tyr Val Lys Gln Cys Gly Gly Thr Thr Arg Ile Phe
       195                 200                 205

Ser Val Thr Asn Gly Gly Gln Glu Arg Lys Phe Val Gly Gly Ser Gly
    210                 215                 220

Gln Val Ser Glu Arg Ile Met Asp Leu Leu Gly Asp Gln Val Lys Leu
225                 230                 235                 240

Asn His Pro Val Thr His Val Asp Gln Ser Ser Asp Asn Ile Ile Ile
                245                 250                 255

Glu Thr Leu Asn His Glu His Tyr Glu Cys Lys Tyr Val Ile Asn Ala
           260                 265                 270

Ile Pro Pro Thr Leu Thr Ala Lys Ile His Phe Arg Pro Glu Leu Pro
       275                 280                 285

Ala Glu Arg Asn Gln Leu Ile Gln Arg Leu Pro Met Gly Ala Val Ile
    290                 295                 300

Lys Cys Met Met Tyr Tyr Lys Glu Ala Phe Trp Lys Lys Lys Asp Tyr
305                 310                 315                 320

Cys Gly Cys Met Ile Ile Glu Asp Glu Asp Ala Pro Ile Ser Ile Thr
                325                 330                 335

Leu Asp Asp Thr Lys Pro Asp Gly Ser Leu Pro Ala Ile Met Gly Phe
           340                 345                 350
```

| | | | | | | | | | | | | | | | |
|---|---|---|---|---|---|---|---|---|---|---|---|---|---|---|---|
| Ile | Leu | Ala | Arg | Lys | Ala | Asp | Arg | Leu | Ala | Lys | Leu | His | Lys | Glu | Ile |
| | | 355 | | | | | 360 | | | | | 365 | | | |
| Arg | Lys | Lys | Lys | Ile | Cys | Glu | Leu | Tyr | Ala | Lys | Val | Leu | Gly | Ser | Gln |
| | 370 | | | | | 375 | | | | | 380 | | | | |
| Glu | Ala | Leu | His | Pro | Val | His | Tyr | Glu | Glu | Lys | Asn | Trp | Cys | Glu | Glu |
| 385 | | | | | 390 | | | | | 395 | | | | | 400 |
| Gln | Tyr | Ser | Gly | Gly | Cys | Tyr | Thr | Ala | Tyr | Phe | Pro | Pro | Gly | Ile | Met |
| | | | | 405 | | | | | 410 | | | | | 415 | |
| Thr | Gln | Tyr | Gly | Arg | Val | Ile | Arg | Gln | Pro | Val | Gly | Arg | Ile | Phe | Phe |
| | | | 420 | | | | | 425 | | | | | 430 | | |
| Ala | Gly | Thr | Glu | Thr | Ala | Thr | Lys | Trp | Ser | Gly | Tyr | Met | Glu | Gly | Ala |
| | | 435 | | | | | 440 | | | | | 445 | | | |
| Val | Glu | Ala | Gly | Glu | Arg | Ala | Ala | Arg | Glu | Val | Leu | Asn | Gly | Leu | Gly |
| | 450 | | | | | 455 | | | | | 460 | | | | |
| Lys | Val | Thr | Glu | Lys | Asp | Ile | Trp | Val | Gln | Glu | Pro | Glu | Ser | Lys | Asp |
| 465 | | | | | 470 | | | | | 475 | | | | | 480 |
| Val | Pro | Ala | Val | Glu | Ile | Thr | His | Thr | Phe | Trp | Glu | Arg | Asn | Leu | Pro |
| | | | | 485 | | | | | 490 | | | | | 495 | |
| Ser | Val | Ser | Gly | Leu | Leu | Lys | Ile | Ile | Gly | Phe | Ser | Thr | Ser | Val | Thr |
| | | | 500 | | | | | 505 | | | | | 510 | | |
| Ala | Leu | Gly | Phe | Val | Leu | Tyr | Lys | Tyr | Lys | Leu | Leu | Pro | Arg | Ser | |
| | | 515 | | | | | 520 | | | | | 525 | | | |

( 2 ) INFORMATION FOR SEQ ID NO:33:

( i ) SEQUENCE CHARACTERISTICS:
       ( A ) LENGTH: 160 base pairs
       ( B ) TYPE: nucleic acid
       ( C ) STRANDEDNESS: both
       ( D ) TOPOLOGY: both ( i i ) MOLECULE TYPE: cDNA ( x i ) SEQUENCE DESCRIPTION: SEQ ID NO:33:

```
TGCAAATACG TAATTAATGC GATCCCTCCG ACCTTGACTG CCAAGATTCA CTTCAGACCA      60

GAGCTTCCAG CAGAGAGAAA CCAGTTAATT CAGCGTCTTC CAATGGGAGC TGTCATTAAG     120

TGCATGATGT ATTACAAGGA GGCCTTCTGG AAGAAGAAGG                            160
```